US007745176B2

(12) United States Patent
Zamost et al.

(10) Patent No.: US 7,745,176 B2
(45) Date of Patent: Jun. 29, 2010

(54) IL-21 PRODUCTION IN PROKARYOTIC HOSTS

(75) Inventors: Bruce L. Zamost, Seattle, WA (US); Douglas C. Covert, Mukilteo, WA (US)

(73) Assignee: ZymoGenetics, Inc., Seattle, WA (US)

( * ) Notice: Subject to any disclaimer, the term of this patent is extended or adjusted under 35 U.S.C. 154(b) by 430 days.

(21) Appl. No.: 11/539,036

(22) Filed: Oct. 5, 2006

(65) Prior Publication Data

US 2007/0048842 A1 Mar. 1, 2007

Related U.S. Application Data

(62) Division of application No. 10/735,149, filed on Dec. 12, 2003, now Pat. No. 7,250,274.

(60) Provisional application No. 60/433,448, filed on Dec. 13, 2002, provisional application No. 60/433,452, filed on Dec. 13, 2002.

(51) Int. Cl.
*C12N 15/09* (2006.01)
*C12P 21/02* (2006.01)

(52) U.S. Cl. .............. 435/69.52; 435/320.1; 435/252.3; 435/325; 435/6; 536/23.5; 530/351

(58) Field of Classification Search ................. None
See application file for complete search history.

(56) References Cited

U.S. PATENT DOCUMENTS

| 6,057,128 A | 5/2000 | Donaldson et al. ......... 435/69.1 |
| 6,307,024 B1 | 10/2001 | Novak et al. ................ 530/351 |
| 6,605,272 B2 | 8/2003 | Novak et al. ............... 424/85.2 |
| 6,686,178 B2 | 2/2004 | Novak et al. ............. 435/69.52 |
| 2005/0124044 A1 | 6/2005 | Cunningham et al. |

FOREIGN PATENT DOCUMENTS

| CN | 1513993 | 4/2003 |
| WO | 03/082212 | 10/2003 |
| WO | 03/087320 | 10/2003 |
| WO | 2005049847 | 6/2005 |

OTHER PUBLICATIONS

U.S. Appl. No. 10/456,780, filed Jun. 6, 2003, Nelson et al.
U.S. Appl. No. 11/539,036, filed Oct. 5, 2006, Zamost et al.
U.S. Appl. No. 11/539,045, filed Oct. 5, 2006, Zamost et al.
U.S. Appl. No. 11/539,055, filed Oct. 5, 2006, Zamost et al.
U.S. Appl. No. 10/456,262, filed Jun. 6, 2003, Nelson et al.
U.S. Appl. No. 11/553,367, filed Oct. 26, 2006, Nelson et al.
U.S. Appl. No. 11/553,381, filed Oct. 26, 2006, Nelson et al.
U.S. Appl. No. 11/553,389, filed Oct. 26, 2006, Nelson et al.
U.S. Appl. No. 11/553,392, filed Oct. 26, 2006, Nelson et al.
U.S. Appl. No. 11/553,395, filed Oct. 26, 2006, Nelson et al.
U.S. Appl. No. 11/548,196, filed Oct. 10, 2006, Nelson et al.
U.S. Appl. No. 11/548,202, filed Oct. 10, 2006, Nelson et al.
U.S. Appl. No. 11/548,517, filed Oct. 11, 2006, Nelson et al.
U.S. Appl. No. 11/548,530, filed Oct. 11, 2006, Nelson et al.
U.S. Appl. No. 11/548,538, filed Oct. 11, 2006, Nelson et al.
U.S. Appl. No. 11/548,554, filed Oct. 11, 2006, Nelson et al.
U.S. Appl. No. 11/548,567, filed Oct. 11, 2006, Nelson et al.
U.S. Appl. No. 11/548,574, filed Oct. 11, 2006, Nelson et al.
U.S. Appl. No. 11/585,538, filed Oct. 11, 2006, Nelson et al.
U.S. Appl. No. 11/548,877, filed Oct. 12, 2006, Nelson et al.
U.S. Appl. No. 11/548,946, filed Oct. 12, 2006, Nelson et al.
U.S. Appl. No. 11/548,963, filed Oct. 12, 2006, Nelson et al.
U.S. Appl. No. 11/548,969, filed Oct. 12, 2006, Nelson et al.
U.S. Appl. No. 11/134,489, filed May 20, 2005, Kindsvogel et al.
U.S. Appl. No. 11/539,479, filed Oct. 6, 2006, Kindsvogel et al.
U.S. Appl. No. 11/539,493, filed Oct. 6, 2006, Kindsvogel et al.
U.S. Appl. No. 11/539,511, filed Oct. 6, 2006, Kindsvogel et al.
U.S. Appl. No. 11/285,970, filed Nov. 23, 2005, Yee.
U.S. Appl. No. 10/659,684, filed Sep. 10, 2003, Novak et al.
U.S. Appl. No. 11/549,772, filed Oct. 16, 2006, Novak et al.
U.S. Appl. No. 11/551,807, filed Oct. 23, 2006, Novak et al.
U.S. Appl. No. 11/551,344, filed Oct. 20, 2006, Novak et al.
U.S. Appl. No. 11/549,868, filed Oct. 16, 2006, Novak et al.
U.S. Appl. No. 11/551,349, filed Oct. 20, 2006, Novak et al.
U.S. Appl. No. 11/551,362, filed Oct. 20, 2006, Novak et al.
U.S. Appl. No. 11/551,368, filed Oct. 20, 2006, Novak et al.
U.S. Appl. No. 11/551,811, filed Oct. 23, 2006, Novak et al.
U.S. Appl. No. 11/551,820, filed Oct. 23, 2006, Novak et al.
U.S. Appl. No. 11/787,442, filed Feb. 26, 20046, Novak et al.
U.S. Appl. No. 11/532,776, filed Sep. 18, 2006, Novak et al.
U.S. Appl. No. 11/551,127, filed Oct. 19, 2006, Novak et al.
U.S. Appl. No. 11/551,136, filed Oct. 19, 2006, Novak et al.
U.S. Appl. No. 11/551,139, filed Oct. 19, 2006, Novak et al.
U.S. Appl. No. 11/551,144, filed Oct. 19, 2006, Novak et al.
U.S. Appl. No. 11/346,580, filed Feb. 2, 2006, Novak et al.
Asano et al., "Antitumor activity of interleukin-21 prepared by novel refolding procedure from inclusion bodies expressed in *Escherichia coli*," *FEBS Letters* 528:70-76, 2002.

*Primary Examiner*—Dong Jiang
(74) *Attorney, Agent, or Firm*—Deborah A. Sawislak; Michelle L. Lewis

(57) ABSTRACT

The expression vectors and methods using an *E. coli* expression system for the large scale production of IL-21 are described. The vectors utilize the IL-21 coding sequence with specific changes in nucleotides in order to optimize codons and mRNA secondary structure for translation in *E. coli*. Using the expression vectors, the IL-21 gene was produced in *E. coli* to a level of greater than 1 g/L in fed batch fermentation. Also included are OmpT deficient *E. coli* strains transformed with an IL-21 expression vector.

11 Claims, 1 Drawing Sheet

IL-21 PRODUCTION IN PROKARYOTIC HOSTS

REFERENCE TO RELATED APPLICATIONS

This application is a divisional of U.S. application Ser. No. 10/735,149, filed Dec. 12, 2003, issued as U.S. Pat. No. 7,250,274. which claims the benefit of U.S. Provisional Application Ser. No. 60/433,448, filed Dec. 13, 2002, and U.S. Provisional Application Ser. No. 60/433,452, filed Dec. 13, 2002, which are herein incorporated by reference.

BACKGROUND OF THE INVENTION

The increased availability and identification of genes from human and other genomes has led to an increased need for efficient expression and purification of recombinant proteins. The expression of proteins in bacteria is by far the most widely used approach for the production of cloned genes. For many reasons, expression in bacteria is preferred to expression in eukaryotic cells. For example, bacteria are much easier to grow than eukaryotic cells. More specifically, the availability of a wealth of sophisticated molecular genetic tools and thousands of mutants make E. coli, as an expression host, extremely useful for protein production. However, the high-level production of functional proteins in E. coli, especially those from eukaryotic sources has often been difficult.

IL-21 (previously designated Zalpha11 Ligand) is a member of the IL-2 family of cytokines that also includes IL-4, IL-7, IL-9, IL-13, and IL-15. Proteins in this family have been shown to have both anti-cancer and anti-viral effects. IL-21 is produced by helper T-cells, which are key regulators of immunity. Based on expression patterns of its cognate receptor and administration of the protein, it has been shown that IL-21 activates $CD8^+$ killer T-cells and natural killer (NK) cells, two classes of lymphocytes that eradicate tumors and virally infected cells. IL-21 also stimulates select classes of B-cells. (Parrish et al., *Nature* 408:57-63, 2000).

Recombinant IL-21 has been produced in prokaryotic cells, in particular E. coli. The resulting bacterial produced protein is not glycosylated, and is produced in an aggregated state. Production of IL-21 from E. coli requires that the aggregated proteins be solubilized from the insoluble inclusion bodies and renatured or refolded. Without renaturation, the specific activity of the recombinant protein will be significantly reduced.

Despite advances in the expression of recombinant proteins in bacterial hosts, there exists a need for improved methods for producing biologically active and purified recombinant IL-21 proteins in prokaryotic systems which result in higher yields for protein production. These and other aspects of the invention will become evident upon reference to the following detailed description. In addition, various references are identified below and are incorporated by reference in their entirety.

SUMMARY OF THE INVENTION

In one aspect, the present invention provides an expression vector for producing IL-21 proteins comprising the operably linked elements of a prokaryotic origin of replication, a transcriptional initiation DNA element, and polynucleotide sequence as shown in SEQ ID NO:27 and a transcriptional terminator. In another aspect, the expression vector is the vector pTAP337. Further embodiments, provide the expression vector can include a selectable marker.

In another aspect, the present invention provides prokaryotic host cells transformed the expression vectors described as comprising SEQ ID NO:27, a polynucleotide sequence encoding the polypeptide of SEQ ID NO:28, or vector pTAP337. In other embodiments, the host strain is E. coli strain W3110 or the strain zGOLD1, deposited with the American Type Culture Collection in Manassas, Va.

In another aspect, the present invention provides methods for producing IL-21 proteins under conditions wherein the IL-21 protein is expressed. In one embodiment, the method comprises culturing a host cell expressing IL-21 after being transformed with pTAP337. In another embodiment, the method comprising culturing a host cell transformed with an expression vector comprising SEQ ID NO:27. The method also comprises recovering the host cells from the growth medium, and then isolating the IL-21 protein from the host cells.

In other aspects, the present invention provides methods for producing IL-21 comprise the steps as described above, in a fed batch fermentation process or a batch fermentation process.

In another aspect, the present invention provides methods for producing an IL-21 protein comprising culturing a host cell as described above in a shake flask to an OD600 of 5 to 20 in a growth medium, inoculating a fermentation vessel with 1 to 12% v/v of shake flask medium containing host cells, culturing the host cells in a growth medium at a pH of 6.2 to 7.2, where a feed solution is fed into the fermentation vessel before 15 hours elapsed fermentation time (EFT), adding an inducing agent to the fermentation vessel at 20 to 30 hours EFT, and harvesting the host cells at 48 to 56 hours EFT. In one embodiment, the inducing agent is isopropyl thiogalactopyranoside (IPTG) at 0.5 to 2 mM. In another embodiment, the feed solution comprises a carbohydrate selected from the group consisting of glycerol and glucose and the feed of is 5 to 15 grams of carbohydrate per hour. In another embodiment, the glycerol in the feed solution is 40 to 70% v/v glycerol or the glucose is 40 to 70% w/v glucose. In further embodiments, the glycerol is about 70% v/v or the glucose is about 60% w/v.

In one aspect, the present invention provides methods of producing IL-21 comprising seeding a flask with an inoculum comprising an E. coli W3110 host cells expressing an IL-21 polypeptide as shown in SEQ ID NO:28, or an E. coli W3110 host cell comprising pTAP337 vector, wherein an IL-21 polypeptide is expressed, and with growth medium comprising about 5 g/l glycerol, culturing the inoculum in a growth medium for 16 to 20 hours at about 30° C., transferring the cultured inoculum in growth medium to a batch fermentator at a concentration 0.5 to 5% v/v inoculum, fermenting the batch fermentation at about 37° C. and about pH 6.8 with about 2% glycerol, introducing a glucose feed at about 8 hours EFT of about 9.5 g glucose/liter/hour and continuing until end of a fermentation run, adding IPTG at about 24 hours EFT to final concentration of 0.5 to 2 mM, fermenting about 28 hours of IPTG, harvesting fermentation broth from the fermentor, adding an equal volume of water to the fermentation broth, and homogenizing and centrifuging to collect a cell pellet or cell slurry comprising IL-21 protein material.

In another aspect, the present invention provides methods for isolating insoluble IL-21 protein comprising a sequence of amino acid residues as shown in SEQ ID NO:28 comprising separating water insoluble IL-21 protein from a cell pellet or slurry, dissolving the insoluble IL-21 material in a chaotropic solvent, diluting the chaotropic solvent and refolding the IL-21 protein; and isolating the IL-21 protein, wherein the isolated IL-21 protein is capable of being biologically active. In one embodiment of the invention, the isolated IL-21 protein is at least 90% pure. In another embodiment, the isolated IL-21 protein is at least 90% pure and has an endotoxin level of less that 10 endotoxin units per mg IL-21 protein.

In another aspect, the present invention provides a method for isolating insoluble IL-21 protein comprising a sequence of amino acid residues as shown in SEQ ID NO:28 comprising separating from a fermentation broth a cell pellet or cell slurry comprising water insoluble IL-21 protein material, homogenizing the cell pellet or cell slurry to collect inclusion bodies, dissolving the insoluble IL-21 protein material in a chaoptropic solvent comprising a guanidine salt, diluting the chaotropic solvent by addition of a refolding buffer comprising arginine salts and a mixture of reducing and oxidizing components, isolating the IL-21 protein by removing unfolded and aggregated proteins by filtering, and purifying the IL-21 refolded protein on a cation exchange column, wherein the isolated and purified IL-21 is capable of being biologically active.

In another aspect, the present invention provides a method for isolating insoluble IL-21 protein comprising a sequence of amino acid residues as shown in SEQ ID NO:28 comprising separating from a fermentation broth a cell pellet or cell slurry comprising water insoluble IL-21 material, homogenizing the cell pellet or cell slurry to collect inclusion bodies, dissolving the insoluble IL-21 protein material in a chaotropic solvent comprising a guanidine salt, diluting the chaotropic solvent by addition of a refolding buffer comprising arginine salts and a mixture of reducing and oxidizing components, isolating the IL-21 protein by removing unfolded and aggregated proteins by filtering, purifying the IL-21 refolded protein on a cation exchange column, and purifying the IL-21 eluate on a hydrophobic interaction column, wherein the isolated and purified IL-21 protein is capable of being biologically active.

In another aspect, the present invention provides a method for isolating insoluble IL-21 protein comprising a sequence of amino acid residues as shown in SEQ ID NO:28 comprising separating from a fermentation broth a cell pellet or cell slurry comprising water insoluble IL-21 protein material, homogenizing the cell pellet or cell slurry to collect inclusion bodies, dissolving the insoluble IL-21 protein material in a chaotropic solvent comprising about 6 M guanidine hydrochloride, 40 mM dithriothreitol (DTT) for about one hour at room temperature, refolding the dissolved inclusion bodies in a solution by diluting into refolding buffer comprising about 2 mM DTT, 4 mM cystine oxidation-reduction pair at least 20 times, adjusting the pH to about 5.5 with about 20% acetic acid and allowing the solution to react for at least five hours, diluting the solution with about 1+1.4 volumes 25 mM acetate, pH 5.5, filtering the solution, loading the solution on a Tosohaas SP-550C resin column equilibrated to pH 5.5 using sodium acetate buffer, washing the resin column with about 0.4 M sodium chloride, washing the resin column with about 0.75 M sodium chloride to elute bound IL-21 protein, adding ammonium sulfate to a concentration of about 1.5 M to eluate and filtering eluate solution, loading eluate solution onto a Tosohaas butyl 650-M column equilibrated to 1.5 M ammonium sulfate, 0.05 sodium chloride in sodium acetate buffer, diluting eluate onto a SP Sepharose HP column equilibrated with sodium acetate buffer, washing column with 20 column volume linear gradient from 0.3 o.7 M sodium chloride, concentration the IL-21 protein, and exchanging buffer to formulation buffer using tangential flow ultrafiltration. In other embodiments, the above methods for isolating insoluble IL-21 protein comprise measuring biological activity using an IL-21 receptor binding assay.

In another aspect, the present invention provides a composition comprising an IL-21 protein comprising a polypeptide as shown in amino acid residues 2-163 of SEQ ID NO:28 at a concentration of about 10 mg/ml IL-21 protein in about 10 mM histidine, 4.7% mannitol at pH 5.3.

DESCRIPTION OF THE INVENTION

Figure 1:
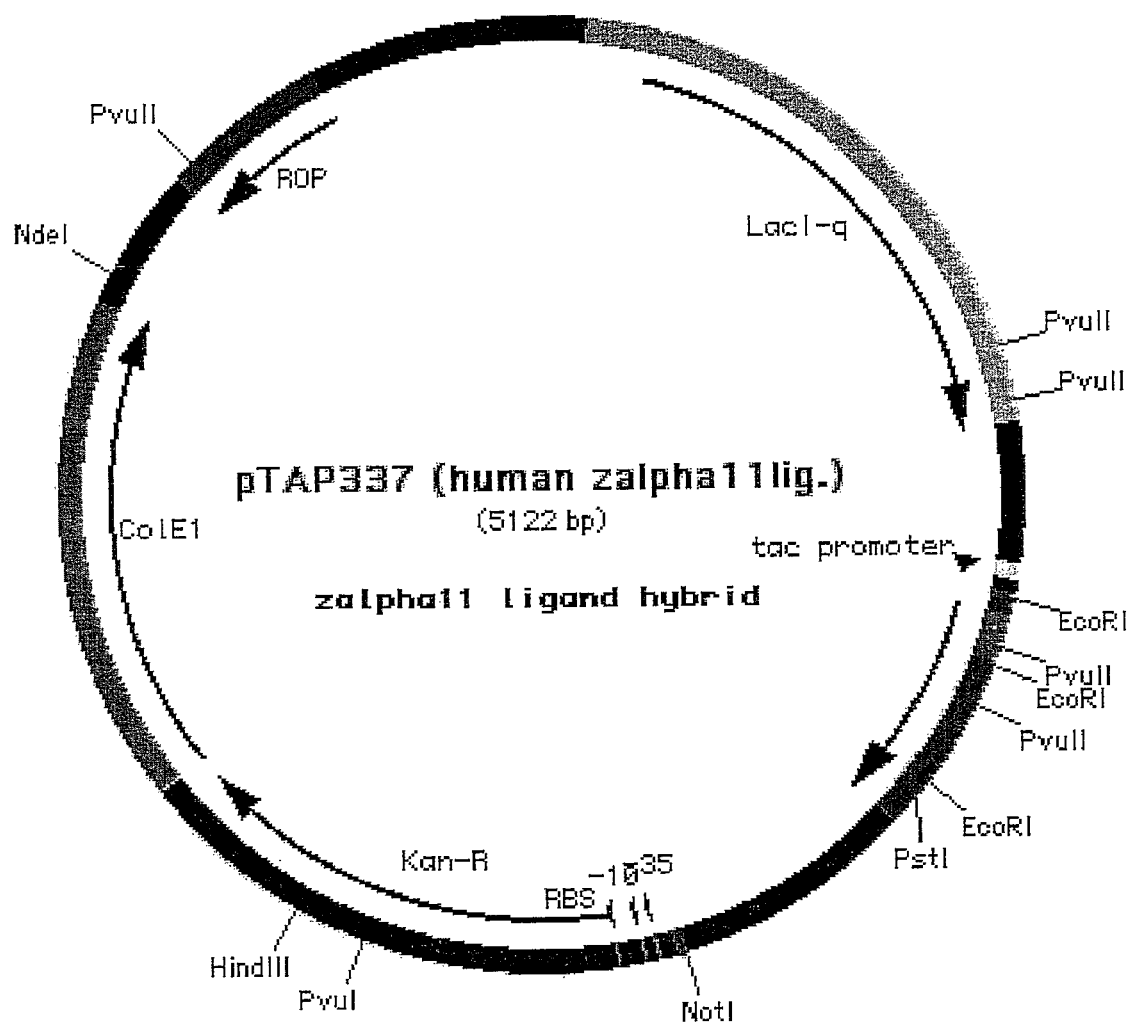
FIG. 1 is illustration of expression plasmid pTAP337, which contains the codon optimized nucleotide sequence for IL-21. The designation of human zalpha11 lig. is IL-21. The plasmid has been deposited with the American Type Culture Collection in Manassas, Va. under Patent Deposit Designation PTA-4853.

The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

"Linear DNA" denotes non-circular DNA molecules with free 5' and 3' ends. Linear DNA can be prepared from closed circular DNA molecules, such as plasmids, by enzymatic digestion or physical disruption.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoters include, for example, but are not limited to, IPTG-inducible promoters, bacteriophage T7 promoters and bacteriophage $\lambda p_L$. See Sambrook et al., *Molecular Cloning: A Laboratory Manual*, 3rd ed., Cold Spring Harbor Laboratory Press, Cold Spring Harbor, N.Y., 2001. A typical promoter will have three components, consisting of consensus sequences at −35 and −10 with a sequence of between 16 and 19 nucleotides between them (Lisset, S. and Margalit, H., *Nucleic Acids Res.* 21: 1512, 1993). Promoters of this sort include the lac, trp, trp-lac (tac) and trp-lac(trc) promoters. If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a eukaryotic regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. Bacterial promoters have regulatory elements that bind and modulate the activity of the core promoter, such as operator sequences that bind activator or repressor molecules.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide resistance to antibiotic.

An "expression vector" is a nucleic acid molecule encoding a gene that is expressed in a host cell. Typically, an expression vector comprises a transcriptional promoter, a gene, an origin of replication, a selectable marker, and a transcriptional terminator. Gene expression is usually placed under the control of a promoter, and such a gene is said to be "operably linked to" the promoter. Similarly, a regulatory element and a core promoter are operably linked if the regulatory element modulates the activity of the core promoter. An expression vector may also be known as an expression construct.

A "recombinant host" is a cell that contains a heterologous nucleic acid molecule, such as a cloning vector or expression vector.

The term "expression" refers to the biosynthesis of a gene product. For example, in the case of a structural gene, expression involves transcription of the structural gene into mRNA and the translation of mRNA into one or more polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein. Proteins are defined herein in terms of their amino acid backbone structures; substituents such as carbohydrate groups and non-peptidic groups are generally not specified, but may be present nonetheless.

A peptide or polypeptide encoded by a non-host DNA molecule is a "heterologous" peptide or polypeptide.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" or "N-terminal" and "carboxyl-terminal" or "C-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "fusion protein" is a hybrid protein expressed by a nucleic acid molecule comprising nucleotide sequences of at least two genes.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, Gene 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

The term "isotonic" is used herein for its conventional meaning, that is a tonicity equal to that of blood, equivalent to a 0.9% solution of NaCl. "An isotonic amount" of a salt is that amount required to make a solution isotonic or to produce an isotonic solution upon reconstitution of a lyophilized preparation.

Concentrations are specified herein in units of molarity or % w/v of liquid compositions. When the composition is in the form of a lyophilized powder, the concentrations of the respective components will be such as to provide the specified concentration on reconstitution of the powder.

Due to the imprecision of standard analytical methods, molecular weights and lengths of polymers are understood to be approximate values. When such a value is expressed as "about" X or "approximately" X, the stated value of X will be understood to be accurate to 110%.

Expression of Recombinant IL-21

The present invention provides expression vectors and methods for producing recombinant IL-21 protein from a prokaryotic host. IL-21 was previously designated zalpha11 Ligand, and is fully described in commonly assigned U.S. Pat. No. 6,307,024, incorporated herein by reference. In particular, the expression vectors and methods of the present invention comprise an *E. coli* expression system for the large scale production of IL-21 utilizing the IL-21 coding sequence with specific changes in nucleotides in order to optimize codons and mRNA secondary structure for translation in *E. coli*. Using the expression vectors and methods of the present invention, the IL-21 gene was produced in *E. coli* to a level of greater than 1 g/L in fed batch fermentation. The present inventors found that use of the *E. coli* OmpT protease deficient strain UT5600 as a production host overcame stability problems with IL-21met. IL-21met is the IL-21 coding sequence with a codon encoding an N-terminal Met added at the 5' end of the polynucleotide sequence. Using the expression vectors described herein significantly improved the yield of recombinant protein recovered from the bacteria. Use of this production host strain yielded over 50 mg/L IL-21met inclusion bodies from shaker flask culture. In another embodiment, to facilitate the development of high cell density fed-batch fermentation, another *E. coli* strain, W3110, was selected as a host for the large scale production of IL-21. This host strain is non-pathogenic and can grow to high cell density in minimally defined fermentation media. The productivity of IL-21met in *E. coli* strain W3110 was comparable to that obtained in *E. coli* strain UT5600 when produced in shaker flask and batch fermentations.

The present invention also provides methods for recovering recombinant IL-21 protein from a prokaryotic host when the IL-21 protein is expressed by the host and found within the host cell as an unglycosylated, insoluble inclusion body. When the prokaryotic cell is lysed to isolate the inclusion bodies (also called refractile bodies), the inclusion bodies are aggregates of IL-21. Therefore, the inclusion bodies must be disassociated and dissolved to isolate the IL-21 protein, and generally this requires the use of a denaturing chaotropic solvent, resulting in recovering a polypeptide that must be refolded to have significant biological activity. Once the IL-21 protein is refolded, the protein must be captured and purified. Thus, the present invention provides for methods for isolating insoluble IL-21 protein from prokaryotic cells, dissolving the insoluble IL-21 protein material in a chaotropic solvent, diluting the chaotropic solvent in such a manner that the IL-21 protein is refolded and isolated. The present invention also includes methods for capturing the renatured IL-21 from the dilute refold buffer using cation exchange chromatography, and purifying the refolded IL-21 protein using hydrophobic interaction chromatography. Further purification is achieved using anion exchange in binding assays using an IL-21 receptor and the like.

The human IL-21 gene encodes a polypeptide of 162 amino acids. The full length sequence includes a signal peptide of 29 amino acids, as shown in SEQ ID NOS:1 and 2, and a mature protein of 133 amino acids comprising residue 30 (Gln) to residue 162 (Ser). The IL-21 sequence as expressed using a prokaryotic expression system has an N-terminal Met, and the nucleotide and corresponding amino acid sequences are shown in SEQ ID NOS: 27 and 28. The nucleotide sequence of SEQ ID NO:27 shows a codon optimized sequence that falls within the scope of the present invention.

Production of recombinant human IL-21 which utilized a mammalian expression system produced approximately 20 mg/L of protein. Therefore, a more cost effective expression system was desirable for large-scale production of IL-21. The *E. coli* system was found to a be a better alternative for large-scale production. One potential Asn-linked glycosylation site is present but not occupied in protein expressed in a CHO cell line using a mammalian expression system or in insect cells using a baculoviral expression system. This structural feature makes IL-21 a good candidate for a prokaryotic expression. Expression in *E. coli* offers numerous advantages over other expression systems, particularly low development costs and high production yields.

Recombinant IL-21 with an N-terminal residue (IL-21met) expressed in *E. coli* was isolated as insoluble inclusion bodies after cell breakage. This material was incorrectly folded and did not possess the desired biological activity. In most cases inclusion bodies needed to be solubilized in denaturing chaotropic solvent and the protein refolded by dilution of the chaotropic agent followed by purification. Proteins vary a great deal with respect to their optimal refolding environment. Factors that can affect the recovery of properly folded and biologically active material include: initial protein concentration, oxidative state, pH, excipients, salts, detergents, termperature, mode of refolding buffer addition and the like. A protein with sequence and structure similarity to IL-21, IL-2, has been expressed in the *E. coli* system and refolded successfully (Weir et al., *J. Biochem.* 245:85, 1987.) ALDESLEUKIN®, a recombinant mutein of human IL-2 has been expressed as inclusion bodies in the *E. coli* system and has been refolded in vitro.

Examination of the codons used in the human IL-21 cDNA indicated that it contained an excess of the least frequently used codons in *E. coli*. Genes with a high content of rarely used codons tend to be expressed at a low level in *E. coli* (Kane, *Curr Opin Biotechnol.* 6(5):494-500, 1995). An additional concern relating to the expression of human IL-21 in *E. coli* was the occurrence of four potential OmpT cleavage sites located in the IL-21 sequence. OmpT is an endopeptidase that specifically cleaves between two consecutive basic residues and the enzyme is active under denaturing conditions such as 8M urea and 6M guanidine-HCl (White et al., *J Biol. Chem.* 270(22):12990-4, 1995; Dekker et al., *Biochemistry* 40(6): 1694-701, 2001). This raises concerns for the stability of 11-21 in a cell extract from *E. coli* due to the proteolytic activity of OmpT.

Several laboratories have shown that the expression level of proteins whose genes contain rare codons can be dramatically improved when the level of certain rare tRNAs is increased within the host (Zdanovsky et al., *Appl Environ Microbiol.* 66(8):3166-73, 2000; Calderone et al., *J Mol. Biol.* 262(4):407-12; Kleber-Janke et al., *Protein Expr Purif.* 19(3): 419-24, 2000; You et al., *Biotechniques.* 27(5):950-4, 1999.) The pRARE plasmid encodes genes for tRNAs that are rare in *E. coli* (argu, argw, leuW, proL, ileX and glyT) with their native promoters (Novy et al., *InNovations,* 12:2-3, 2001). Co-expression with pRARE enhanced IL-21met production in *E. coli* by about 5-10 fold. Co-expression with pRARE also decreased the level of truncated IL-21met in *E. coli* cell lysate, suggesting that re-synthesizing the IL-21met gene with more appropriate codons would be beneficial.

The present invention provides an expression vector comprising the coding sequence of Il-21 with codons optimized for translation in *E. coli*. The synthetic gene encoding IL-21met was obtained by overlap PCR. The final PCR product was introduced into an expression vector for expression under the control of the Tac promotor. However, expression was low. An examination of the secondary structure of the IL-21met cDNA revealed an exceptionally stable hairpin structure. It was suspected that this hairpin loop was the structural element that prevented efficient expression from the fully optimized sequence. When the hairpin structure was eliminated by replacing the first eighty bases of the optimized sequence with the sequence as shown in SEQ ID NO: 1. The hybrid IL-21 is shown in SEQ ID NO: 27, and the resulting gene was expressed in *E. coli* at high levels. Expression levels with the new expression construct increased to around 20% of total cell protein or 100 mg/L.

Expression vectors that are suitable for production of a desired protein in prokaryotic cells typically comprise (1) prokaryotic DNA elements coding for a bacterial origin for the maintenance of the expression vector in a bacterial host; (2) DNA elements that control initiation of transcription, such as a promoter; (3) DNA elements that control the processing of transcripts, such as a transcriptional terminator, and (4) a gene encoding a selectable marker, such as antibiotic resistance. The prokaryotic host cell produces IL-21 upon introduction of an expression vector and addition of an appropriate inducer. Accordingly, the present invention contemplates expression vectors comprising a promoter, the IL-21 optimized nucleotide sequence, and a terminator sequence. The exemplary optimized IL-21 nucleotide sequence is shown in SEQ ID NO:27. In another embodiment, the expression vector further comprises a selectable marker. In one embodiment, the selectable marker is kanamycin resistance.

Expression vectors can also comprise nucleotide sequences that encode a peptide tag to aid in purification of the desired protein. Peptide tags that are useful for isolating recombinant polypeptides include, for example, polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329: 215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

One of ordinary skill in the art will be familiar with a multitude of molecular techniques for the preparation of the expression vector. For example, the IL-21 polynucleotide can be prepared by synthesizing nucleic acid molecules using mutually priming, long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology Vol. 15: PCR Protocols: Current Methods and Applications*, White (ed.), pages 263-268, (Humana Press, Inc. 1993), and Holowachuk et al., *PCR Methods Appl.* 4:299 (1995)).

Another method for constructing expression systems utilizes homologous recombination using a yeast system. See U.S. Pat. No. 6,207,442, Plasmid Construction by Homologous Recombination, incorporated herein by reference. The system provides a universal acceptor plasmid that can be used to clone a DNA encoding any polypeptide of interest, including polypeptide fusions. The system provides methods for preparing double stranded, circular DNA molecules comprising a region encoding a protein of interest. One or more donor DNA fragments encoding the protein of interest, i.e., IL-21, are combined with an acceptor plasmid, a first DNA linker, and a second DNA linker in a *Saccharomyces cerevisiae* host cell whereby the donor DNA fragment is joined to the acceptor plasmid by homologous recombination of the donor DNA, acceptor plasmid, and linkers to form the closed, circular plasmid.

The nucleic acid molecules of the present invention can also be synthesized with "gene machines" using protocols such as the phosphoramidite method. If chemically-synthesized, double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

Examples of alternate techniques that can be used to prepare the IL-21 gene and expression vector include, for example, restriction endonuclease digestion and ligation, and polymerase chain reaction, all of which are well known in the art.

A wide variety of selectable marker genes is available (see, for example, Kaufman, *Meth. Enzymol.* 185:487 (1990); Kaufman, *Meth. Enzymol.* 185:537 (1990)). It is common for expression vectors to comprise selection markers, such as tetracycline resistance, amplicillin resistance, kanamycin resistance, neomycin resistance, or chlormaphenicol resistance. A selectable marker will permit selection and/or detection of cells that have been transformed with expression vector from cells that have not been transformed. An expression vector can carry more than one such antibiotic resistance gene. An example of selectable marker without antibiotic resistance uses the hok/sok system from plasmid R1. The hok gene encodes the toxic Hok protein of 52 amino acids and the sok gene encodes an antisense RNA, which is complementary to the hok mRNA leader sequence. This selectable marker is known to one skilled in the art and is described in more detail by Gerdes, K. et al., *Genetic Engineering*, 19:49-61, 1997.

A wide variety of suitable recombinant host cells is encompassed by the present invention and includes, but is not limited to, gram-negative prokaryotic host organisms. Suitable strains of *E. coli* include W3110, K12-derived strains MM294, TG-1, JM-107, BL21, and UT5600. Other suitable strains include: BL21(DE3), BL21(DE3)pLysS, BL21(DE3) pLysE, DH1, DH4I, DH5, DH5I, DH51F', DH51MCR, DH10B, DH10B/p3, DH11S, C600, HB101, JM101, JM105, JM109, JM110, K38, RR1, Y1088, Y1089, CSH18, ER1451, ER1647, *E. coli* K12, *E. coli* K12 RV308, *E. coli* K12 C600, *E. coli*HB101, *E. coli* K12 C600 R.sub.k-M.sub.k–, *E. coli* K12 RR1 (see, for example, Brown (ed.), *Molecular Biology Labfax* (Academic Press 1991)). Other gram-negative prokaryotic hosts can include *Serratia, Pseudomonas, Caulobacter*. Prokaryotic hosts can include gram-positive organisms such as *Bacillus*, for example, *B. subtilis* and *B. thuringienesis*, and *B. thuringienesis* var. *israelensis*, as well as *Streptomyces*, for example, *S. lividans, S. ambofaciens, S. fradiae*, and *S. griseofuscus*. Suitable strains of *Bacillus subtilus* include BR151, YB886, M1119, M1120, and B170 (see, for example, Hardy, "*Bacillus* Cloning Methods," in *DNA Cloning: A Practical Approach*, Glover (ed.) (IRL Press 1985)). Standard techniques for propagating vectors in prokaryotic hosts are well-known to those of skill in the art (see, for example, Ausubel et al. (eds.), *Short Protocols in Molecular Biology*, 3$^{rd}$ *Edition* (John Wiley & Sons 1995); Wu et al., *Methods in Gene Biotechnology* (CRC Press, Inc. 1997)). For an overview of protease deficient strains in prokaryotes, see, Meerman et al., *Biotechnology* 12:1107-1110, 1994. The present invention is exemplified using the W3110 strain, which has been deposited at the American Type Culture Collection (ATCC) as ATCC # 27325.

Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987. Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient that is complemented by the selectable marker carried on the expression vector or co-transfected into the host cell. Liquid cultures are provided with sufficient aeration by conventional means, such as shaking of small flasks or sparging of fermentors. Transformed cells can be selected and propagated to provide recombinant host cells that express the gene of interest. IL-21 can be expressed in *E. coli* using the MBP (maltose binding protein) fusion system (New England Biolabs (NEB; Beverly, Mass.)). In this system, the IL-21 cDNA is attached to the 3' end of the malE gene to form an MBP-IL-21 fusion protein. Fusion protein expression is driven by the tac promoter and is "off" until the promoter is induced by addition of 1 mmol IPTG (isopropyl b-thiogalactosylpyranoside). The constructs can be built as in-frame fusions with MBP in accordance with the Multiple Cloning Site (MCS) of the pMAL-c2 vector (NEB), and according to the manufacturer's specifications.

Fermentation

In one embodiment of the present invention a batch fermentation can be used, particularly when a large scale production of IL-21 using the expression system of the present invention is required. Generally, batch fermentation comprises that a first stage seed flask is prepared by growing *E. coli* strains expressing IL-21 in a suitable medium in shake flask culture to allow for growth to an optical density (OD) of 5 to 20 at 600 nm. A suitable medium would contain nitrogen from a source(s) such as ammonium sulfate, ammonium phosphate, ammonium chloride, yeast extract, hydrolyzed animal proteins, hydrolyzed plant proteins or hydrolyzed caseins. Phosphate will be supplied from potassium phosphate, ammonium phosphate, phosphoric acid or sodium phosphate. Other components would be magnesium chloride or magnesium sulfate, ferric sulfate or ferric chloride, and other trace elements. Growth medium can be supplemented with carbohydrates, such as fructose, glucose, galactose, lactose, and glycerol, to improve growth. In certain embodiments, carbohydrate additions would be glycerol or glucose added from 1 to 20 g/L medium. In certain embodiments, the glycerol or glucose is 5-10 g/L. Growth is started by inoculating a shake flask (baffled flask from 500 ml to 2000 ml) containing a preferred growth medium with *E. coli* from an agar medium containing antibiotic, for example kanamycin at 10-50 µg/ml, at the appropriate concentration or from a frozen stock culture. Growth in the shake flasks is at a temperature between 28 and 40° C. In certain embodiments, the shake flasks are grown at 30 to 37° C. The flasks are incubated with agitation set at 200 to 300 rpm.

Fermentation vessels are prepared with a suitable growth medium and sterilized. The pH of the medium is adjusted to a pH 6.5 to 7.5. In certain embodiments, the pH is 6.8, 6.9, 7.0, 7.1 or 7.2. The vessels are set to the proper aeration and agitation levels and inoculated from a first stage seed flask culture that has been grown 10 to 20 hours and has an OD of 5 to 20 at 600 nm. The inoculation level is between 1% and 12% volume/volume (v/v). In certain embodiments, the inoculation level is at 3%, 4%, 5%, 6%, 7%, 8%, 9% or 10% v/v. The dissolved oxygen level is maintained above 20% saturation by increasing agitation speed, increasing the aeration rate, sparging in oxygen, or various combinations. The culture is grown until the OD 600 reaches 2 to 20OD units at 600 nm. Isopropyl thiogalactopyranoside (IPTG) is then added to the culture to a concentration 0.1 to 2.0 mM. The IPTG induces the tac promoter to express the IL-21. Alternatively, lactose at 30% solution can be added at 10 g/l at 24 hours for induction. The culture is then allowed to grow for an additional time between 2 and 8 hours. In certain embodiments, the culture is grown for 3-4 hours.

In another embodiment, a fed batch culture is used to generate a high yield of IL-21 protein. The IL-21 producing *E. coli* strains are grown in a suitable medium in shake flask culture to allow for growth to an OD of 5 to 20 at 600 nm. A suitable medium would contain nitrogen from a source(s) such as ammonium sulfate, ammonium phosphate, ammonium chloride, yeast extract, hydrolyzed animal proteins, hydrolyzed plant proteins or hydrolyzed caseins. Phosphate will be supplied from potassium phosphate, ammonium phosphate, phosphoric acid or sodium phosphate. Other components would be magnesium chloride or magnesium sulfate, ferric sulfate or ferric chloride, and other trace elements. Growth medium can be supplemented with carbohydrates such as fructose, glucose, galactose, lactose and glycerol, to improve growth. In certain embodiments, carbohydrate additions would be glycerol or glucose added from 1 to 40 g/L medium. In one embodiment, the glycerol or glucose is 5-10 g/L. Growth is started by inoculating a shake flask (baffled flask from 500 ml to 2000 ml) containing a preferred growth medium with *E. coli* from an agar medium containing kanamycin (10-50 µg/ml) or from a frozen stock culture. Growth in the shake flasks is at a temperature of 28 to 40° C. In certain embodiments, growth temperature is 30 to 37° C. The flasks are incubated with agitation set at 200 to 300 rpm.

A second stage vessel is prepared with a suitable growth medium and sterilized. A suitable medium would be, for example, Super Broth II (Becton Dickenson, Franklin Lakes, N.J.), APS-Super Broth, Luria Broth, or ZSM (see, Tables 1-4) and kanamycin. Growth medium can be supplemented with carbohydrates to improve growth. Certain embodiments provide carbohydrate additions that have glycerol or glucose added from 1 to 40 g/L medium. In one embodiment, glycerol or glucose is 5-10 g/L. The pH of the medium is adjusted to a pH of 6.5 to 7.5. In certain embodiments, the pH is 6.8, 6.9, 7.0, 7.1 or 7.2. The vessels are set to the proper aeration and agitation levels. Growth is started by inoculating the vessel from a first stage seed flask culture that has been grown 10 to 20 hours and has an OD of 5 to 20 at 600 nm. The inoculation level is 1% to 12% v/v. In certain embodiments, the induction level will be 3%, 4%, 5%, 6%, 7%, 8%, 9% or 10% v/v. The dissolved oxygen level is maintained above 20% saturation by increasing agitation speed, increasing the aeration rate, sparging in oxygen or various combinations thereof.

Fermentation vessels are prepared with a suitable growth medium (as described above) and sterilized. The pH of the medium is adjusted to a pH between 6.2, 6.3, 6.4, 6.5, 6.6, 6.7, 6.8, 6.9, 7.0, 7.1 or 7.2. In one embodiment, the medium is adjusted to pH 6.8. Growth medium can be supplemented with carbohydrates to improve growth. In some embodiments, carbohydrate additions are glycerol or glucose added from 5 to 40 g/L medium with certain embodiments having glycerol or glucose at 15-20 g/L. The vessels are set to the proper aeration and agitation levels and inoculated from a first stage seed flask culture or second stage seed vessel that has been grown to 10 to 20 hours and has an OD of 5 to 20 at 600 nm. The inoculation level is between 1% and 12% v/v. In certain embodiments, the inoculation level is 5%, 6%, 7%, 8%, 9% or 10% v/v. The dissolved oxygen level is maintained above 20% saturation by increasing agitation speed, increasing the aeration rate, sparging in oxygen or various combinations thereof.

A carbohydrate solution is fed into the fermentor at a pre-determined rate starting at the beginning of the fermentation run, but generally after 6 hours elapsed fermentation time (EFT), and no longer than 12 hours EFT. The feed is continued until the end of the fermentation. The feed solution can be glycerol prepared at 40-70% v/v or glucose prepared at 40-70% weight/volume (w/v). In certain embodiments, glycerol or glucose are prepared at 70% v/v glycerol and 60% w/v glucose. Feed rates can vary between 5-15 grams of glucose or glycerol per liter per hour. In one embodiment the feed rate is 8, 9, or 10 g/L/hr. At a time of 20 to 30 hours EFT, for example at 24 hours, IPTG is added to the culture to a concentration of 0.5 to 2 mM. Alternatively, lactose at 30% solution can be added at 10 g/l at 24 hours for induction. At a time of 48 to 56 hours EFT, the fermentation is harvested. Alternatively, an additional 0.5 to 2 mmol/L of IPTG is added to the fermentor culture. The fermentation is then harvested at 52 to 56 hours EFT.

At the end of the fermentation run the temperature is adjusted downward to from 4° to 20° C., and the pH is either maintained or adjusted to 5.0 to 9.0. In certain embodiments, the range is 6.0 to 8.0 pH units. The fermentation broth is harvested by over-pressurization of the vessel and collection of the broth through the sample port. Alternatively, the broth can be pumped out through one of the sample ports. The fermentation broth can contain 10%-30% w/v solids.

IL-21 Recovery

Following fermentation the cells are harvested by centrifugation, re-suspended in homogenization buffer and homogenized, for example, in an APV-Gaulin homogenizer (Invensys APV, Tonawanda, N.Y.) or other type of cell disruption equipment, such as bead mills and sonicators. Alternatively, the cells are taken directly from the fermentor and homogenized in an APV-Gaulin homogenizer. Alternatively, the fermentation broth may be diluted with water or buffer prior to homogenization.

In one embodiment, the cells are homogenized directly in the fermentation broth. For example, an APV-Gaulin 1000 or APV-Gaulin 2000 homogenizer is chilled to 4°-15° C. for at least 30 minutes. The fermentation broth is passed through the homogenizer and the cell suspension is collected. The homogenizer pressure should be set at 6000 to 14,000 psi for maximum cell disruption. In one embodiment, the pressure is set for 10,000 psi. The suspension is passed through the homogenizer between 1-5 times, for example, for 3 passes. In another embodiment, the broth is diluted with an equal volume of water prior to homogenization. The amount of DNA may be decreased by the addition of PEI, spermine or benzonase during or after the homogenization step.

The homogenate is centrifuged, and the pellet containing the inclusion bodies is obtained after decanting the supernatant. The inclusion body pellet is washed in water, or Tris buffers with or without varying levels of the following compounds: sodium chloride, urea, Triton X-100, zinc chloride, sodium lauryl sulfate, sucrose.

In another embodiment, the cells are harvested by transferring the fermentation broth to centrifuge bottles and centrifuging at 2-8° C. for 20-60 minutes. For example, a Beckman J6MI centrifuge with KompSpin KAJ7.100 rotor (Beckman Coulter, Fullerton, Calif.) at 7500×G can be used to harvest cells. A Beckman Avanti JHC centrifuge with a Beckman JLA-8.1 fixed angle rotor (8,800×G) or an Aries JS 5.0 Swinging Bucket rotor with 2.25 L bottles at 7500×G can be used as well. A continuous centrifuge such as those supplied by Carr Separations, Inc. (Franklin, Mass.) or Westfalia Separator, Inc. (Northvale, N.J.) can also be used.

The culture broth or supernatant is removed from the centrifuge bottles. The cell pellets are resuspended in homogenization buffer (100 mM Tris, 5 mM $ZnCl_2$, pH 7.5) at 10-30% w/v solids. The fermentation broth is passed through the APV-Gaulin homogenizer and the cell suspension is collected. The homogenizer pressure should be set at 6000-14,000 psi for maximum cell disruption. In one embodiment, the pressure is 10,000 psi. The suspension is passed through the homogenizer for 1-5 passes, for example, 3 passes.

Additionally, the methods of recovering IL-21 can comprise a further step of precipitating, washing, and resolubilizing the IL-21. The washed inclusion bodies are solubilized in 6 M guanidine or 8 M urea, diluted 6-10 fold in water or buffer, incubated 30 minutes, and centrifuged or filtered. Alternatively, ultrafiltration or macrofiltration can be used wash inclusion bodies after homogenization. The resulting precipitate is washed in 2-6 M urea, and contains the IL-21 protein. The precipitate is then washed with water prior to solubilization. Addition of $Al^{3+}$ or $Fe^31$ or anionic and cationic polymers or agents such as spermine, PEI and benzonase may be added to precipitate cell debris, soluble proteins, DNA, RNA, and carbohydrates.

Solubilization of Inclusion Bodies

The washed inclusion body prep can be solubilized using guanidine hydrochloride (5-8 M), guanidine thiocyanate (5-6 M), or urea (7-8 M) containing a reducing agent such as beta mercaptoethanol (10-100 mM), or dithiothreitol (5-50 mM). The solutions can be prepared in Tris, phosphate, HEPES or other appropriate buffers. Inclusion bodies can also be solubilized with urea (2-4 M) containing sodium lauryl sulfate (0.1-2%). Inclusion bodies from 1 liter of fermentation broth can be solubilized using 50-200 ml of the described solutions. The one method provides solubilizing the inclusion body pellets from 1 liter of fermentation broth in 150 ml of 6 M GuHCl prepared in 100 mM Tris, pH 8.0, containing 40 mM DTT. In another embodiment, an inclusion body slurry is mixed with 50-100 ml 8 M GuHCL. The slurry is re-suspended by mixing with a spatula followed by homogenization with an Omni EZ homogenizer (Omni International, Warrenton, Va.) or mixing with a mechanical device. The suspension is mixed for 30-120 minutes, at 3-37° C. In one embodiment, the suspension is mixed at 15-25° C., to finish the solubilization process. The sample is then centrifuged at 7,000×G at 4° C. for 10-30 minutes using an appropriate centrifuge. The supernatant sample containing the solubilized IL-21 is decanted and retained.

The concentration of the IL-21 in the solubilized fraction is determined by reversed phase HPLC. A Jupiter C5 column (Phenomenex, Torrance, Calif.) is used with acetonitrile/trifluoroacetic acid as the mobile phase. IL-21 standard is diluted in a guanidine/DTT/Tris-containing buffer and different amounts are injected onto the column. The area under the IL-21 peak is used to construct a standard curve. The solubilized IL-21 sample is microfuged to remove particulates prior to injection on the HPLC column. Determination of the area under the IL-21 peak allows quantification of the IL-21 concentration from the standard curve.

Additionally, the solubilized IL-21 may be purified at this stage using tangential flow filtration, reverse phase HPLC of immobilized metal affinity chromatography.

Refolding

In one aspect of the invention, the process for recovering purified IL-21 from transformed *E. coli* host strains in which the IL-21 is expressed as refractile inclusion bodies, the cells are disrupted and the inclusion bodies are recovered by centrifugation.

The inclusion bodies are then solubilized and denatured in 6 M guanidine hydrochloride containing a reducing agent. The reduced IL-21 is then oxidized in a controlled renaturation step. This step involves dilution in a refold buffer containing arginine hydrochloride, salts, and an oxido-shuffling system. The oxido-shuffling system is used to initiate disulfide bonding of the IL-21 molecule, and is based on mixtures of reduced and oxidized molecules such as cysteine and cystine, DTT and cystine, reduced glutathione and oxidized glutathione, and DTT and oxidized glutathione. The ratio of reduced to oxidized glutathione can range from 1:1 to 6:1 with a concentration range of 0.5 and 8 mM. In one embodiment, the optimal concentration is 4 mM reduced glutathione: 2 mM oxidized glutathione. The ratio of cysteine to cystine can range from 2:1 to 1:1 with a concentration range of 4 mM to 1 mM of either reagent. In one embodiment, the optimal concentration is 4 mM cysteine, with 2 mM cystine. Optimal refolding may also be achieved using 4 mM cystine and 2 mM DTT which form 4 mM cysteine and 2 mM cystine. Refolding may also be done by sulfitolysis in the presence of reagents such as sodium sulfite and sodium tetrathionate. The renatured IL-21 is captured from the dilute refold buffer using cation exchange chromatography, and is purified using hydrophobic interaction chromatography and high performance cation exchange chromatography.

The solute containing IL-21 is added rapidly (1-5 minutes), or slowly (0.5-5 hours) to the refolding buffer with mixing. The refolding buffer contains arginine (0.5 to 1.25 M), PEG, and salts. It may also include glycerol, guanidine HCl, urea, EDTA, protease inhibitors and chaperones, alcohol, detergents, glycerol and copper sulfate. The IL-21 can be added in one addition, in multiple additions, or fed in over time. The IL-21 is added to the refolding mixture to a final concentration of 0.05 to 1.2 mg/ml. The temperature range is 4-30° C. The pH is 7.3 to 8.5. The vessel containing the refold mixture is left open to the atmosphere or can be sparged with air or nitrogen during renaturation. The refolding is allowed to take place 1 to 26 hours.

Refolding can also be done in the presence of EDTA to decrease methionine oxidation, or on a size exclusion column, or using tangential flow filtration, or electrodialysis.

Clarification and Concentration of Refolded IL-21

Refolded IL-21 is adjusted to pH 5.5 and then passed through a 1.2 µm filter for clarification and removal of insoluble protein. The filtered solution is concentrated 10-30 fold using tangential flow filtration on a plate and frame system or with a hollow fiber cartridge. The concentrate is then diluted 3-10 fold with buffer or water to allow unfolded and aggregated proteins to precipitate. The solution is then passed through a filter for clarification and removal of insoluble protein.

Alternatively, the refolded IL-21 is diluted 2-fold to 10-fold in water or 25 mM sodium acetate, pH 5.5. A precipitate or flocculent forms and, after approximately 30 minutes to five hours, is removed by filtration. A 1.2 µm nominal filter followed by a 0.45 μm nominal filter, or a depth filter with a positive zeta potential, can be used to remove the flocculent. It would be possible to use other filters such as a graded density filter. It is also possible to use centrifugation or microfiltration to remove the flocculent.

Capture of IL-21

In another aspect of the present invention, after the IL-21 protein is refolded and concentrated, the methods of the present invention comprise capturing the refolded IL-21 protein is captured in dilute buffer on a cation exchange column and purifying IL-21 protein using hydrophobic interaction chromatography and high performance cation exchange chromatography.

The capture step is designed to capture the diluted, folded IL-21 and carry out initial purification. In order for IL-21 to bind to the column a dilution is first carried out. The clarified, diluted IL-21 is captured on a cation exchange column at pH 5.5. Typically, SP Sepharose XL (Amersham Biosciences, Piscataway, N.J.) or TOYOPEARL SP 550C (Tosoh Biosep, Montgomery, Pa.) is used. The equilibration buffer is 25 mM sodium acetate, 0.2 to 0.45 M sodium chloride, pH 5.5, and the bound IL-21 is eluted with an increasing salt gradient. IL-21 elutes from the SP Sepharose XL at approximately 0.6 M sodium chloride and from the TOYOPEARL SP 550C at approximately 0.8 M sodium chloride.

Expanded bed chromatography can also be used for IL-21 capture following refolding. In that case the dilution step is carried out in-line while loading the IL-21 onto the column. Streamline SP XL (Amersham Biosciences) is equilibrated with 25 mM sodium acetate, 0.2 M NaCl, pH 5.5. IL-21 is then loaded in upflow mode onto the equilibrated Streamline SP XL resin, which is maintained at twice the settled bed height, while diluting 1:3 inline with water. Following washing in both upflow and downflow modes, IL-21 is eluted in downflow mode with a 0.6 M NaCl step or a NaCl gradient.

The methods of the present invention provide the use of many different cation exchange resins for this step, including weak cation exchangers such as carboxymethyl, different types of solid supports such as agarose or cellulose, and different particle sizes. The methods of the present invention can also provide running the columns at different pHs in the range from 5.0 to 7.0, and with different buffers and salts. Alternatively, other chromatographic methods such as hydrophobic interaction, anion exchange, and metal chelate maybe used to capture the refolded IL-21.

Purification

In one aspect of the present invention, there is an intermediate purification of IL-21 protein. This step is designed to achieve further purification of the IL-21 using hydrophobic interaction chromatography. Typically Butyl Sepharose FF (Amersham Biosciences) or TOYOPEARL butyl 650M (Tosoh Biosep) are resins used for this step. The resin is equilibrated with 25 mM sodium acetate, 50 mM NaCl, 1.5 M $(NH_4)_2SO_4$, pH 5.5. IL-21 that has been purified by cation exchange chromatography is adjusted to 1.5 M $(NH_4)_2SO_4$ and then passed through a 0.45 μm nominal filter. The adjusted and filtered IL-21 is then loaded onto the equilibrated resin, which is then washed with equilibration buffer to remove unbound material. IL-21 is eluted with a gradient to 25 mM sodium acetate, 50 mM NaCl, pH 5.5. IL-21 elutes from the column at approximately 0.75 M $(NH_4)_2SO_4$ to 0.3 M $(NH_4)_2SO_4$.

Other hydrophobic interaction chromatography resins that can be used for this step include, for example, those substituted with phenyl or hexyl, different types of solid supports such as agarose or cellulose, and different particle sizes. The present invention also provides running the columns at different pHs in the range from 5.0 to 9.0, and with different buffers and salts. The present invention also provides running the column in such a manner that IL-21 does not bind.

The IL-21 is further purified by high performance cation exchange chromatography. Typically, the IL-21 is diluted to a conductivity of 30 ms/cm, adjusted to pH 6.0 with 0.5 M dibasic phosphate and loaded onto a column of Sepharose SP HP (Amersham Biosciences). The column is equilibrated with 25 mM sodium phosphate, 0.3 M sodium chloride, pH 6.0. It is washed with equilibration buffer and then IL-21 is eluted with a sodium chloride gradient. The present invention also provides using other high performance cation exchange resins. The columns can be run at different pH values in the range from 5.0 to 7.5 with different buffers, such as phosphate. The load material can be diluted with water or buffer to conductivity values in the range from 5 to 35 ms/cm.

The methods for purifying IL-21 can comprise concentrating and carrying out a buffer exchange of the protein. This step is designed to concentrate the high performance cation exchange column eluate and exchange it into formulation buffer. The final column eluate pool is concentrated approximately 10 fold using a 5 kDa molecular weight cut-off tangential flow filtration plate and frame membrane, diafiltered against phosphate buffered saline, pH 6.0, or against 10 mM histidine, 4.72% (w/v) mannitol, pH 5.0, 5.1, 5.2 or 5.3, then concentrated a second time to further increase the concentration of IL-21.

Other membranes can be used, such as a 3 kDa or 8 kDa molecular weight cut-off plate and frame membrane or a 10 kDa molecular weight cut-off hollow fiber system to achieve this ultrafiltration/diafiltration step. The purity of the IL-21 following high performance cation exchange chromatography is at least 95%, and typically greater than 98%, by sodium dodecyl sulfate polyacrylamide gel electrophoresis. The endotoxin level in the IL-21 preparation following cation exchange chromatography capture, hydrophobic interaction chromatography purification, and buffer exchange, is generally <10 endotoxin units per mg IL-21 protein, and typically <2 endotoxin units per mg IL-21 protein. The endotoxin level following high performance cation exchange chromatography is generally <1 endotoxin unit per mg IL-21.

Analysis of material produced using Streamline SP XL and butyl Sepharose FF (without the 20-fold concentration prior to the cation exchange chromatography) showed that aggregates are less than 0.2% by size exclusion HPLC, the charge heterogeneity by cation exchange HPLC is approximately 10%, and the purity measure by reversed phase HPLC is approximately 90%. Analysis of material produced using Toyopearl SP 550C, Toyopearl butyl 650 M and Separose SP HP showed that aggregates are less than 2% by size exclusion HPLC, purity by reversed phase HPLC is approximately 90%, and charge heterogeneity measure by cation exchange HPLC is approximately 4%.

Further purification of IL-21 to remove the remaining impurities and contaminants may be desirable. For example, an anion exchange column can be used to reduce the endotoxin level. IL-21 is diluted to a conductivity level of <10 mS/cm and the pH is adjusted to 8.0. It is applied to a Q Sepharose FF column (Amersham Biosciences) which has been equilibrated to 20 mM Tris, pH 8.0. The IL-21 passes through the column and has an approximately 80% reduction in endotoxin compared to the load. Mustang Q or Mustang E (Pall, Port Washington, N.Y.) membranes can also be used to reduce endotoxin levels between pH 5.0 and 9.0.

Other purification steps that could potentially be used to further purify IL-21 include metal chelate chromatography, anion exchange chromatography, or hydrophobic interaction chromatography on a phenyl column. It is also possible to carry out purification prior to refolding the IL-21, using for example reversed phase HPLC, ion exchange chromatography or metal chelate chromatography. Thus, the present invention further provides methods comprising the additional steps of purification disclosed herein.

Characterization of Purified IL-21

BaF3 is an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986). BaF3 cells expressing the full-length 11-21 receptor have been constructed as described fully in U.S. Pat. No. 6,307,024. This cell line that is dependent on the IL-21 receptor-linked pathway for survival, and culturing the cell line in the absence of other growth factors can be used to assay for biologically active IL-21. Proliferation of the BaF3/IL-21R cells can be assessed by using various dilutions of purified IL-21 protein which are added to the cells and comparing growth of the treated cells to growth of cells grown in the absence of IL-21 protein.

Assays measuring cell proliferation or differentiation are well known in the art. For example, assays measuring proliferation include such assays as chemosensitivity to neutral red dye (Cavanaugh et al., *Investigational New Drugs* 8:347-354, 1990, incorporated herein by reference), incorporation of radiolabeled nucleotides (Cook et al., *Analytical Biochem.* 179:1-7, 1989, incorporated herein by reference), incorporation of 5-bromo-2'-deoxyuridine (BrdU) in the DNA of proliferating cells (Porstmann et al., *J. Immunol. Methods* 82:169-179, 1985, incorporated herein by reference), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses*, 161-171, 1989; all incorporated herein by reference). IL-21 produced by the methods described herein is capable of stimulating proliferation of BaF3/IL-21 R cells.

Purified IL-21 can be characterized by a number of physical methods. Optimally, amino acid analysis indicates the amino acid composition of all residues is within 10% of the expected values. N-terminal sequencing gives a single sequence beginning with methionine and corresponding to the sequence predicted from the IL-21 expression vector. Whole mass analysis using mass spectrometry gives a value within 0.01% of the predicted mass of IL-21 (15593.84 Da). Endoproteinase Lys C digestion followed by liquid chromatography-mass spectrometry can be used to generate a peptide map in which all peaks correspond in mass to predicted tryptic peptides in IL-21, and in which all predicted tryptic peptides from IL-21 are identified. Peptide mapping also indicates disulfide bonding consistent with that predicted for a protein that is a member of the IL-2 family, as well as an absence of methionine oxidation Formulation The pH was selected to minimize degradation observed by SE-HPLC (soluble dimer formation, content loss), CIE-HPLC (apparant deamidation), and RP-HPLC (oxidation and degradation by pathways yet to be identified). In certain embodiments, the range of pH is 5.0-5.6 using a histidine buffer based on buffer capacity, stability, and parenteral administration compatibility. Alternatively, citrate or succinate buffers may be used. In one embodiment, mannitol was selected as a tonicity adjuster (isotonic solution) on the basis of stability, and compatibility with lyophilization. In other embodiments, sorbitol or glycine can be used. NaCl can be used, but may be less stable. Trehalose or sucrose can be used, but may potentially hydrolize under these slightly acidic conditions. However, formulations may include from 1 mg/ml to 100 mg/ml IL-21 in the formulation. In one embodiment, IL-21 protein is formulated at a concentration of 10 mg/mL IL-21 in 10 mM histidine, 4.7% w/v mannitol, pH 5.3. The product was stored frozen at −20 C. Determination of whether a solution product is viable depends on the specification limits which are deemed acceptable, and those skilled in the art will define limits to maximize product recovery, minimize aggregation, minimize charge heterogeneity, minimize impurities and maintain acceptable biological activity. When limits of <3% dimer (high molecular weight), >90% purity by CIE- and RP-HPLC, and >90% label claim of content were set, a refrigerated solution product was stable and considered a reasonable alternative. Doses of IL-21 between 0.1 to 3 mg/kg will generally not exceed 30 ml for IV bolus delivery.

A lyophilized product can also be prepared and would fall with the scope of the present invention. Other excipients may also be included in the compositions of the present invention. For example, acceptable excipients include disaccharides, such as trehalose and sucrose at 0.5% to 10% as stabilizers; polyethylene glycol at 0.001% to 0.1% as a stabilizer or wetting agent; surfactants, such as tween 20, tween 80 or triton-X-100 at 0.001% to 0.1% as a stablizer or wetting agent; or other bulking agents, such as glycine, hydroxyethyl starch in the range of 0.5% to 5%.

Stability studies may be done under accelerated conditions such as storage at elevated temperature of 25° C. to 45° C. or agitation. For example, multiple freeze-thaw cycles were done, with the IL-21 formulation shown to be stable at concentrations of 20 mg/ml. In one embodiment, pH 5.25 is used to reduce rates of degradation. However, an optimal pH range for lypholized product is 4.75 to 7.5, with non-lyophilized products in the pH range of 5 to 5.6.

One or more preservatives may also be included in the compositions of the present invention, particularly in those compositions packaged for multiple use. Preservatives that can be used within the present invention include those commonly used in pharmaceutical preparations, such as methylparaben, propylparaben, benzyl alcohol, m-cresol, ethylmercurithiosalycilate, phenol, thimerosal, and the like.

L-21 compositions intended for pharmaceutical use will be sterile and pyrogen-free, and will be manufactured and packaged according to accepted pharmaceutical procedures. The compositions can be packaged in unit dosage or multiple dosage quantities. The compositions will typically be packaged in sealed glass vials with polytetrafluoroetylene-lined stoppers and with appropriate labeling. Lyophilized compositions may be packaged as a kit that includes an appropriate quantity of a suitable diluent, such as water for injection (WFI) or 5% dextrose in WFI.

The invention is further illustrated by the following non-limiting examples.

EXAMPLES

Example 1

Construction of Expression Vector, pTAP237

Plasmid pTAP237 was generated by inserting a PCR-generated linker into the SmaI site of pTAP186 by homologous recombination. Plasmid pTAP186 was derived from the plasmids pRS316 (a *Saccharomyces cerevisiae* shuttle vector) and pMAL-c2, an *E. coli* expression plasmid derived from pKK223-3 and comprising the tac promoter and the rrnB terminator. Plasmid pTAP186 contains a kanamycin resistance gene in which the Sma I site has been destroyed and has NotI and SfiI sites flanking the yeast ARS-CEN6 and URA3 sequences, facilitating their removal from the plasmid by digestion with NotI. The PCR-generated linker replaced the expression coupler sequence in pTAP186 with the synthetic RBS II sequence. It was prepared from 100 pmoles each of oligonucleotides zc29,740 and zc29,741, as shown in SEQ ID NOS: 3 and 4, respectively, and approximately 5 pmoles each of oligonucleotides zc29,736 and zc29,738, as shown in SEQ ID NOS: 5 and 6, respectively. These oligonucleotides were combined by PCR for ten cycles of 94° C. for 30 seconds, 50° C. for 30 seconds, and 72° C. for 30 seconds, followed by 4° C. soak. The resulting PCR products were concentrated by precipitation with two times the volume of 100% ethanol. Pellet was resuspended in 10 μL water to be used for recombining into the recipient vector pTAP186 digested with SmaI to produce the construct containing the synthetic RBS II sequence. Approximately 1 μg of the PCR-generated linker and 100 ng of pTAP186 digested with SmaI were mixed together and transformed into competent yeast cells (*S. cerevisiae*). The yeast was then plated onto –URA D plates and left at room temperature for about 72 hours. Then the Ura+ transformants from a single plate were resuspended in 1 mL H$_2$O and spun briefly to pellet the yeast cells. The cell pellet was resuspended in 0.5 mL of lysis buffer. DNA was recovered and transformed into *E. coli* MC1061. Clones were screened by colony PCR as disclosed above using 20 pmoles each of oligonucleotides zc29,740 and zc29,741, as shown in SEQ ID NOS: 3 and 4, respectively. Clones displaying the correct size band on an agarose gel were subject to sequence analysis. The correct plasmid was designated pTAP237.

Example 2

Construction of pTAP252

The human IL-21 coding sequence (as shown in SEQ ID NO:1) was generated by PCR amplification using a CD3+ cDNA library pool as template and oligonucleotide primers zc29,084 and zc22,127 (SEQ ID NOS: 7 and 8, respectively). To optimize the translation process in *E. coli*, primer zc29,084 (SEQ ID NO:7) added an ATG initiation codon to the 5' end of the IL-21 coding sequence. The resulting gene sequence encoded the mature IL-21 with one extra methionine at the N-terminus (IL-21met). The final PCR product was inserted into expression vector pTAP237 (described in Example 1) by yeast homologous recombination (Raymond et al., *Biotechniques*. 26(1):134-8, 140-1, 1999; U.S. Pat. No. 6,027,442, incorporated herein by reference). The expression construct, pTAP252, was extracted from yeast and transformed into competent *E. coli* MC1061. Kanamycin resistant clones were identified by colony PCR. A positive clone was verified by sequencing and subsequently transformed into either production host strain E104 or UT5600.

Example 3

Codon Optimization

Induction of expression of human IL-21met from pTAP252 produced about 2-5% of total cellular protein in *E. coli* strain E104. Examination of the codons used in the IL-21 coding sequence indicated that it contained an excess of the least frequently used codons in *E. coli* with a CAI value equal to 0.181. The CAI is a statistical measure of synonymous codon bias and can be used to predict the level of protein production (Sharp et al., *Nucleic Acids Res.* 15(3):1281-95, 1987). Genes coding for highly expressed proteins tend to have high CAI values (>0.6), while proteins encoded by genes with low CAI values (<0.2) are generally inefficiently expressed. This suggested a reason for the poor production of IL-21 in *E. coli*. Additionally, the rare codons are clustered in the second half of the message leading to higher probability of translational stalling, premature termination of translation, and amino acid misincorporation (Kane J F. *Curr. Opin. Biotechnol.* 6(5):494-500, 1995).

It has been shown that the expression level of proteins whose genes contain rare codons can be dramatically improved when the level of certain rare tRNAs is increased within the host (Zdanovsky et al., ibid., 2000; Calderone et al., ibid., 1996; Kleber-Janke et al., ibid., 2000; You et al., ibid., 1999). The pRARE plasmid carries genes encoding the tRNAs for several codons that are rarely used *E. coli* (argU, argW, leuW, proL, ileX and glyT). The genes are under the control of their native promoters (Novy, ibid.) Co-expression with pRARE enhanced IL-21met production in *E. coli* by about 5-10 fold. Co-expression with pRARE also decreased the level of truncated IL-21met in *E. coli* lysate. These data suggest that re-resynthesizing the gene coding for IL-21met with more appropriate codon usage provides an improved vector for expression of large amounts of IL-21.

The codon optimized IL-21met coding sequence was constructed from sixteen overlapping oligonucleotides: zc22,913 (SEQ ID NO:9), zc22,914 (SEQ ID NO:10), zc22,915 (SEQ ID NO: 11), zc22,916 (SEQ ID NO:12), zc22,961 (SEQ ID NO: 13), zc22962 (SEQ ID NO:14), zc22,963 (SEQ ID NO: 15), zc22,964 (SEQ ID NO: 16), zc22,965 (SEQ ID NO:17), zc22,966 (SEQ ID NO:18), zc22,968 (SEQ ID NO:20), zc22,969 (SEQ ID NO:21), zc22,967 (SEQ ID NO:19), zc22,970 (SEQ ID NO:22), zc22,971 (SEQ ID NO:23), and zc22,972 (SEQ ID NO:24). Primer extension of these overlapping oligonucleotides followed by PCR amplication produced a full length IL-21met gene with codons optimized for expression in *E. coli*. The final PCR product was inserted into expression vector pTAP168 by yeast homologous recombination. The expression construct was extracted from yeast and transformed into competent *E. coli* MC1061. Clones resistance to kanamycin were identified by colony PCR. A positive clone was verified by sequencing and subsequently transformed into either production host strain E104 or UT5600. The expression vector with the optimized IL-21met sequence was named pTAP196. The final PCR product was introduced into vector pTAP168 for expression under the control of Tac promotor. However, the expression was very low and the product could only be detected by Western analysis using monoclonal antibodies directed against IL-21 as the probe.

Examination of the secondary structure of the IL-21met message revealed an exceptionally stable hairpin structure in the region between bases 36 and 64 (SEQ ID NO:1). It was suspected that this structural element prevented efficient translation from the IL-21met message. Therefore, a hybrid IL-21 met coding sequence was generated by overlap PCR. A fragment containing the first eighty bases of the non-optimized IL-21met sequence was generated by PCR amplification using pTAP252 as template and oligonucleotide primers zc29,740 (SEQ ID NO:3) and zc40, 133 (SEQ ID NO:25). The optimized region of IL-21met from base 81 to 450 (SEQ ID NO:27) was generated by PCR amplification using pTAP196 as template and oligonucleotide primers zc22,971 (SEQ ID NO:23) and zc40, 107 (SEQ ID NO:26). These two PCR products were combined and amplified using oligonucleotide primers zc22,971 (SEQ ID NO:23) and zc29,740 (SEQ ID NO:3) to generate full length IL-21met by overlap PCR. The final PCR product was inserted into expression vector pTAP237 by yeast homologous recombination. The expression construct was extracted from yeast and transformed into competent E. coli MC1061. Clones resistant to kanamycin were identified by colony PCR. A positive clone was verified by sequencing and subsequently transformed into either production host strain E104 or UT5600. The expression vector with the hybrid IL-21met coding sequence was named pTAP337.

Once the hairpin structure was eliminated by replacing the first eighty bases of the optimized sequence with the first eighty nucleotides of the non-optimized IL-21met sequence (shown in SEQ ID NO:1), the resulting gene was expressed very well in E. coli. Expression levels with the new construct increased to around 20% of total cell protein.

Example 4

Expression of IL-21met

E. coli were inoculated into 100 mL Superbroth II medium (Becton Dickinson, Franklin Lakes, N.J.) containing 0.01% Antifoam 289 (Sigma-Aldrich, St. Louis, Mo.) and 30 µg/ml kanamycin, and cultured overnight at 37° C. A 10 mL inoculum was added to 500 mL of same medium in a 2 L culture flask that was shaken at 275 rpm at 37° C. until the culture attained an OD600 of 4. IPTG was then added to a final concentration of 1 mM and shaking was continued for another 2.5 hours. The cells were centrifuged at 4,000×g for 10 min at 4° C. The cell pellets were frozen at −80° C. for use at a later time.

Expression of IL-21met was performed on a larger scale in a 25 mL culture at 37° C. One mL of culture was collected 2 hours after IPTG induction. E. coli cells were resuspended in an equal volume BugBuster® Protein Extraction Reagent (Novagen, Madison, Wis.) at 4° C. and incubated for 20 min. The soluble and insoluble fractions were separated by centrifugation at 16,000×g for 10 min at 4° C.

Recombinant IL-21met accumulated as insoluble inclusion bodies. The recovery yield of IL-21met from most of the E. coli strains was considered low. About 80 to 90% of IL-21met in the inclusion bodies was lost within 20 min after cell lysis and incubation at 4° C. Lysing bacteria with 8 M urea did not improve recovery. However, including protease inhibitors, such as 5 mM $ZnCl_2$ and 0.5 mM Benzamidine, in the cell lysis buffer prevented the loss of IL-21met from strain E104 (W3110 arabinose⁻). This indicated that a bacterial protease capable of cleaving IL-21met under denaturing conditions was co-purifying with the inclusion bodies. It was observed that IL-21met was stable in cells lysates from strain UT5600, but not in E104 cell lysates. This suggested that the protease was present in E104 but not UT5600. Comparison of the genotypes of these strains revealed that OmpT, which cleaves between dibasic residues, was present in E104 but not in UT5600. OmpT is heat stable and active even under denaturing conditions (White et al., ibid. 1995). Examination of the amino acid sequence of IL-21 indicated that it contained at least four potential OmpT cleavage sites. IL-21met also demonstrated excellent stability in BL21, another OmpT deficient E. coli strain. These data suggested that OmpT protease activity was critical for the stability and recovery of IL-21. The use of E. coli strain UT5600 as the production host significantly improves the recovery of IL-21met. Overall the yields of IL-21met were increased from 2 mg/L to 50-100 mg/L with the combination of construct and host strain improvement.

Example 5

Characterization of IL-21

For Western analysis, protein samples were separated on a 4-20% MES-SDS NuPAGE gel (Invitrogen) under reducing conditions and transferred to nitrocellulose membrane (Invitrogen) at 30 V for 1 hour. The membrane was blocked with 5% non-fat milk in TTBS buffer (20 mM Tris pH 7.4, 160 mM NaCl, 0.1% Tween 20). Polyclonal antibody specific for human IL-21 was added in TTBS Buffer with 5% non-fat milk and incubated for 1 hour. After washing with TTBS, the blot was probed with HRP conjugated goat-anti rabbit IgG (Bio-Rad) for 1 hour. The blot was subsequently washed three times with TTBS before chemiluminescent detection with ECL reagent from Pierce.

Example 6

Plasmid Stability Analysis

E. coli was inoculated into 25 mL Superbroth II medium (Becton Dickinson) containing 0.01% Antifoam 289 (Sigma) and 30 µg/ml kanamycin, and cultured overnight at 37° C. A 25 µL inoculum was added to 25 mL of same medium without kanamycin in a 25 mL culture flask which was shaken at 275 rpm at 37° C. 100 µL of culture were collected at four different time points (when the culture reached OD600 values of 2, 4, 6 and 8). The samples were diluted and plated on LB agar plates without any additives. After overnight incubation at 37° C., 100 E. coli colonies were replica plated onto a LB agar plate and a LB agar plate containing 30 µg/ml kanamycin. After overnight incubation at 37° C., the number of colonies that formed on each plate was counted and compared. The number of colonies that grew on LB plus kanamycin relative to the number that grew on the plate without antibiotic reflected the percentage of cells still harboring the expression vector.

When clones of W3110 carrying the pTAP337 expression vector were cultured for 12 hours in medium that did not contain kanamycin, more than 90% retained the plasmid. Clones carrying the expression vector without the IL-21 gene showed similar retention of the plasmid. These data demonstrate that the pTAP337 expression vector carrying IL-21 is stable in W3110.

E. coli strains, TG1 and MM294, were not selected as the production host due to low productivity of IL-21 and serious plasmid instability. The most encouraging results came from the studies using E. coli strain W3110 (ATCC #27325) to produce IL-21. The productivity of W3110 was comparable to that of UT5600. Plasmid stability studies demonstrated that the expression vector, pTAP337, was maintained in W3110 as well. UT5600 is an auxotrophic strain and more difficult to grow at large scale. These considerations led to selection of W3110 as the preferred host strain for production of IL-21.

Example 7

Batch Fermentation

A first stage seed flask (baffled 500 ml flask with 100 ml medium) was prepared with Difco APS Super Broth (Difco Laboratories, Detroit, Mich.), supplemented with glycerol at 5 g/L and kanamycin at 25 ug/ml. Growth was started by inoculating the shake flask with a loop full of *E. coli* W3110 containing the expression vector pTAP 337 (EE410) from a 24 hour old agar plate (Luria agar (Difco Laboratories) containing kanamycin 25 µg/ml). Growth in the shake flask was at a temperature of 30° C. The flask was incubated with agitation set at 250 rpm.

A 6 L fermentation vessel was prepared with 3.0 L of Difco APS Super Broth and sterilized. The growth medium was supplemented with glycerol at 10 g/L and kanamycin at 25 µg/ml. The pH of the medium was adjusted to 7.2. Aeration of the vessel was set to 1 vvm and agitation was set at 350 rpm. The temperature was set to 37° C. The fermentor was inoculated from a first stage seed flask culture grown for 16 hours to an optical density (OD) of 16 at 600 nm. The inoculation was 5% v/v. Dissolved oxygen was maintained above 20% saturation by increasing agitation speed.

The culture was grown until the OD600 reached 2.5 (approx 2.5 hours). Isopropyl thiogalactopyranoside (IPTG) was added to the culture to a concentration of 1.0 mM. The culture was then allowed to grow for an additional 3 hours.

Example 8

A. Fed Batch Fermentation

A first stage seed flask (baffled 500 ml flask with 100 ml medium) was prepared with Difco APS Super Broth, supplemented with glycerol at 5 g/L and kanamycin at 25 ug/ml. Growth was started by inoculating the shake flask with a loop full of *E. coli* W3110 containing the expression vector pTAP 337 (described above) from a 24 hour old agar plate (Luria agar containing kanamycin 25 µg/ml). The shake flask was incubated at 30° C. with agitation set at 250 rpm.

A 6 L fermentation vessel was prepared with 3.0 L of ZymoM growth medium and sterilized. The growth medium was supplemented with glycerol at 20 g/L and kanamycin at 25 µg/ml. The pH of the medium was adjusted to pH 6.4. Aeration was set to 1 vvm, agitation to 350 rpm, and temperature to 32° C. The fermentor was inoculated from a first stage seed flask culture that had been grown for 16 hours to an OD600 of 16. Inoculation was 5% v/v and dissolved oxygen was maintained above 20% saturation by increasing agitation speed.

A carbohydrate solution was fed into the fermentor starting at 10 hours EFT. The feed was continued until the end of the fermentation. The feed solution was glycerol prepared at 70% v/v. The feed rate was 6 grams of glycerol per liter per hour based on the initial starting volume. At 24 hours EFT, IPTG was added to the culture to a concentration of 2 mM. At 48 hours EFT, the fermentation was harvested.

In an alternative fed batch process, a first stage seed flask (baffled 500 ml flask with 100 ml medium) was prepared with ZSM, supplemented with glucose at 20 g/L and kanamycin at 25 µg/ml. Growth was started by inoculating the shake flask with 300 µl *E. coli* W3110 frozen in 20% glycerol and containing the expression vector pTAP337. The culture was incubated at 30° C. with agitation at 250 rpm.

A 6 L fermentation vessel was prepared with 3.0 L of ZymoM growth medium and sterilized. The growth medium was supplemented with glucose at 20 g/L and kanamycin at 25 µg/ml. The pH of the medium was adjusted to 6.8. Aeration was set to 1 vvm, agitation to 350 rpm, and temperature to 37° C. The fermentor was inoculated from a first stage seed flask culture that had been grown for 16 hours to an OD600 of 16. Inoculation was 5% volume/volume and the dissolved oxygen level was maintained above 20% saturation by increasing agitation speed.

A carbohydrate solution was fed into the fermentor starting at 10 hours EFT. The feed was continued until the end of the fermentation. The feed solution was glucose prepared at 60% v/v and the feed rate was 9.5 grams of glucose per liter per hour based on the initial starting volume. At 24 hours EFT, IPTG was added to the culture to a concentration of 2 mM. At 48 hours EFT, 2 mmol/l of IPTG was added to the culture bringing the IPTG concentration to 4 mM. The fermentation was harvested at 56 hours.

TABLE 1

| ZSM medium (shake flask and seed fermentor) | |
|---|---|
| Ingredient | Amt g/L or ml/L |
| Yeast Extract | 5.0 |
| Sodium Sulfate dibasic | 2.0 |
| Ammonium Sulfate dibasic | 2.5 |
| Ammonium Chloride | 0.5 |
| Potassium Phosphate dibasic | 14.6 |
| Potassium Phosphate monobasic | 3.6 |
| Di water | 1.0 L |
| After autoclaving add: | |
| 60% Glucose | 20 g/L (33 mL) |
| Trace D sol. | 3 mL |
| 1M MgSO4 | 3 mL |
| Kanamycin (25 mg/mL stock concentration) | 1.0 mL |

TABLE 2

| 60% glucose solution for fed batch | |
|---|---|
| Ingredient | Amt g/L |
| H2O | 800 mL |
| Glucose | 1200 g |
| Adjust volume with H2O to: | 2.0 L |
| After autoclaving add: | |
| 1M MgSO4 (30 mL/L) | 60 mL |

TABLE 3

| ZymoM - (fed batch fermentation medium) | |
|---|---|
| Ingredient | Amount g/L or ml/L |
| (NH4)2SO4 | 14.0 |
| KH2PO4 | 2.0 |
| K2HPO4 | 16.5 |
| Yeast Extract | 5.5 |
| Glycerol | 20.0 |
| Antifoam AF208 | 0.1 mL |
| Conc. H3PO4 | 1.5 |
| DI water | 1.0 L |
| After autoclaving add: | |
| 1M MgSO4 | 10 mL |
| Trace D Solution* | 17.0 mL |
| Kanamycin (25 mg/mL stock concentration) | 1 mL |

TABLE 4

Trace "D" Solution (for ZymoM and ZSM media)

| Ingredient | Amt. g/L |
| --- | --- |
| FeCl3.6H2O | 6.48 |
| ZnSO4.7H2O | 1.68 |
| MnCl2.4H2O | 1.20 |
| Na2MoO4.2H2O | 0.50 |
| CuSO4.5H2O | 0.24 |
| H3BO3 | 0.72 |
| Conc. H3PO4 | 48.0 mL |
| dH2O | 1.0 L |

B. Fed Batch Fermentation with PCOL22 Medium

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain EE410 (*E. coli* W3110 containing the expression vector pTAP337). The shake flask was incubated at 32 C with agitation set to 250 rpm.

A 6 L fermentation vessel was prepared with 2.7 L of PCOL22 medium and sterilized. After cooling the growth medium was supplemented with, glucose at 20 g/L, magnesium sulfate, calcium chloride, and kanamycin at 25 μg/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an OD600 nm of 16. Inoculation was 5% v/v and dissolved oxygen was maintained above 20% saturation by increasing agitation speed. pH was controlled at 6.8 by addition of 5 N $NH_4OH$.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

C. Fed Batch Fermentation with PCOL22 Medium Minus Kanamycin

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain EE410 (*E. coli* W3110 containing the expression vector pTAP337). The shake flask was incubated at 32 C with agitation set to 250 rpm.

A 6 L fermentation vessel was prepared with 2.7 L of PCOL22 medium and sterilized. After cooling the growth medium was supplemented with, glucose at 20 g/L, magnesium sulfate, and calcium chloride. No kanamycin was added. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an OD600 nm of 16. Inoculation was 5% v/v and dissolved oxygen was maintained above 20% saturation by increasing agitation speed. pH was controlled at 6.8 by addition of 5 N $NH_4OH$.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

D. Fed Batch Fermentation with PCOL22-L Medium

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain EE410 (*E. coli* W3110 containing the expression vector pTAP337). The shake flask was incubated at 32 C with agitation set to 250 rpm.

A 6 L fermentation vessel was prepared with 2.7 L of PCOL22-L medium and sterilized. This medium contains citric acid and has one-third less-salts to prevent precipitation. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an OD600 nm of 16. Inoculation was 5% v/v and dissolved oxygen was maintained above 20% saturation by increasing agitation speed. pH was controlled at 6.8 by addition of 5 N $NH_4OH$.

A glucose solution (60% w/v) minus magnesium sulfate was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

E. Fed Batch Fermentation with PCOL12-L Medium

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain EE410 (*E. coli* W3110 containing the expression vector pTAP337). The shake flask was incubated at 32 C with agitation set to 250 rpm.

A 6 L fermentation vessel was prepared with 2.7 L of PCOL22-L medium and sterilized. This medium contains ¼th less-salts to prevent precipitation. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an OD600 nm of 16. Inoculation was 5% v/v and dissolved oxygen was maintained above 20% saturation by increasing agitation speed. pH was controlled at 6.8 by addition of 5 N $NH_4OH$.

A glucose solution (60% w/v) minus magnesium sulfate was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

F. Fed Batch Fermentation with PCOL 12-R Medium

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain EE410 (*E. coli* W3110 containing the expression vector pTAP337). The shake flask was incubated at 32 C with agitation set to 250 rpm.

A 6 L fermentation vessel was prepared with 2.7 L of PCOL22-R medium and sterilized. This medium contains increased levels of yeast extract and glucose to increase the growth of the host strain before glucose feeding is initiated. After cooling the growth medium was supplemented with, glucose at 40 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an OD600 nm of 16. Inoculation was 5% v/v and dissolved oxygen was maintained above 20% saturation by increasing agitation speed.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

G. Fed Batch Fermentation in 20 L Vessel

In an alternative fed batch process, a first stage seed vessel (6 l) was prepared with 3.0 L of ZSM medium, supplemented with glucose at 20 g/L and kanamycin at 25 ug/ml. Growth was started by inoculating the vessel with 3.0 ml of material from a thawed frozen vial containing the production strain EE410 (*E. coli* W3110 containing the expression vector pTAP337). Aeration was set to 1 vvm, agitation was set to 350 rpm, and temperature to 32° C.

A 20 L fermentation vessel was prepared with 10.8 L of PCOL22 medium and sterilized. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from the first stage seed vessel culture of EE410 that had been grown for 16 hours to an OD600 nm of 16. Inoculation was 5% v/v and dissolved oxygen was maintained above 20% saturation by increasing agitation speed. Culture pH was controlled at 6.8 through addition of 5N ammonium hydroxide.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

H. Fed Batch Fermentation with 2 Stage Seed

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain EE410 (*E. coli* W3110 containing the expression vector pTAP337). The shake flask was incubated at 32 C with agitation set to 250 rpm.

A second stage seed vessel (6 l) was prepared with 3.0 L of ZSM medium, supplemented with glucose at 20 g/L and kanamycin at 25 ug/ml. Growth was started by inoculating the vessel with 100 ml of material from a first stage seed flask containing the production strain EE410 (*E. coli* W3110 containing the expression vector pTAP337). Aeration was set to 1 vvm, agitation was set to 350 rpm, and temperature to 32° C.

A 20 L fermentation vessel was prepared with 10.8 L of PCOL22 medium and sterilized. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a second stage seed vessel that had been grown for 12 hours to an OD600 nm of 16. Inoculation was 5% v/v and dissolved oxygen was maintained above 20% saturation by increasing agitation speed. Culture pH was controlled at 6.8 through addition of 5N ammonium hydroxide.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

I. Fed Batch Fermentation with ZGOLD1

Construction of the expression vector zGOLD1 is described in Example 19. A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain *E. coli* W3110 ompT-(ZGOLD1) containing the expression vector pTAP337). The shake flask was incubated at 32 C with agitation set to 250 rpm.

A 6 L fermentation vessel was prepared with 2.7 L of PCOL22 medium and sterilized. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an OD600 nm of 16. Inoculation was 5% v/v and dissolved oxygen was maintained above 20% saturation by increasing agitation speed. Culture pH was controlled at 6.8 through addition of 5N ammonium hydroxide.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

TABLE 5

PCOL22 Production Medium

| Ingredient | Amt. g/L or ml/L |
|---|---|
| (NH4)2SO4 | 14.0 |
| KH2PO4 | 2.0 |
| K2HPO4 | 16.5 |
| Antifoam AF208 | 0.1 mL |
| DI water | 0.920 L |
| After autoclaving add: | |
| 1M MgSO4 | 10 mL |
| Trace D Solution* | 34.0 mL |
| Kanamycin (25 mg/mL stock concentration) | 1 mL |
| 1 M CaCl$_2$—2H$_2$O | 2 mL |
| Glucose (60% w/v) | 33.0 ml |

TABLE 6

PCOL22-L Medium

| Ingredient | Amt. G/L or ml/L |
|---|---|
| (NH4)2SO4 | 9.25 |
| KH2PO4 | 1.32 |
| K2HPO4 | 10.90 |
| Citric Acid | 1.0 g |
| Antifoam AF204 | 0.1 mL |
| DI water | 0.920 L |
| After autoclaving add: | |
| 1M MgSO4 | 10 mL |
| Trace D Solution* | 34.0 mL |
| Kanamycin (25 mg/mL stock concentration) | 1 mL |
| 1 M CaCl$_2$—2H$_2$O | 2 mL |
| Glucose (60% w/v) | 33.0 ml |

60% glucose for fed batch using PCOL22-L and PCOL 12 L medium

TABLE 7

60% glucose for fed batch using PCOL22-L and PCOL 12 L medium

| Ingredient | Amt g/L |
|---|---|
| H2O | 800 ml |
| Glucose (60% w/v) | 1200 g |
| Adjust volume with H2O to: | 2.0 L |
| Autoclave | |

TABLE 8

PCOL12-R Medium

| Ingredient | Amt. G/L or ml/L |
|---|---|
| (NH4)2SO4 | 14.0 |
| KH2PO4 | 2.0 |
| K2HPO4 | 16.5 |
| Yeast Extract | 20.0 |
| Antifoam AF204 | 0.1 mL |
| DI water | 0.920 L |
| After autoclaving add: | |
| 1M MgSO4 | 10 mL |
| Trace D Solution* | 34.0 mL |
| Kanamycin (25 mg/mL stock concentration) | 1 mL |
| 1 M CaCl$_2$—2H$_2$O | 2 mL |
| Glucose (60% w/v) | 66.0 ml |

TABLE 9

PCOL12-L Medium

| Ingredient | Amt. g/L or ml/L |
|---|---|
| (NH4)2SO4 | 10.5 |
| KH2PO4 | 1.50 |
| K2HPO4 | 12.4 |
| Yeast Extract | 5.0 |
| Antifoam AF204 | 0.1 mL |
| DI water | 0.920 L |
| After autoclaving add: | |
| 1M MgSO4 | 10 mL |
| Trace D Solution* | 34.0 mL |
| Kanamycin (25 mg/mL stock concentration) | 1 mL |
| 1 M CaCl$_2$—2H$_2$O | 2 mL |
| Glucose (60% w/v) | 33.0 ml |

Example 9

IL-21 Recovery

A. Disruption of Harvested Cells

The harvested *E. coli* pellet was produced by fed-batch fermentation, and contained approximately 5-6 g/L of IL-21met in inclusion body form. The fermentation broth (1 L) was pelleted by centrifugation at 8000×g for 30 minutes The pellet was resuspended in 850 ml of breakage buffer (100 mM Tris, pH 7.2, 5 mM ZnCl$_2$) and chilled on ice. The broth was passed through the APV homogenizer three times at 10,000 psi. The broth was then centrifuged at 8000×g for 30 minutes. The supernatant was discarded, taking care to retain the loose pellet. The pellet was washed twice by resuspension in 800 ml of DI water and centrifugation at 8000×g for 40 minutes. The supernatant was discarded, taking care to retain the loose pellet. The inclusion body pellet was stored at −80° C. or refolded without freezing.

B. Direct Disruption of Harvested Broth

The harvested *E. coli* broth was produced by fed-batch fermentation, and contained approximately 6-7 g/L of IL-21met in inclusion body form. The fermentation broth (0.5 L) was diluted to 1.0 L with deionized water and passed through the APV homogenizer three times at 10,000 psi. The broth was then centrifuged at 15,000×g for 30 minutes. The supernatant was discarded, taking care to retain the loose pellet. The pellet was resuspended in 500 ml of DI water and centrifuged at 15,000×g for 30 minutes. The supernatant was discarded, taking care to retain the loose pellet. The washing step was repeated and the inclusion body pellet was stored at −80° C. or refolded without freezing.

C. Solubilization and Precipitation

1. Solubilization was achieved by suspension of the washed inclusion body pellet in 200 mL of 100 mM Tris, 6 M Guanidine hydrochloride, 5 mM ZnCl$_2$, pH 7.2 at room temperature for one hour. The suspension was then centrifuged at 12000 g for 30 minutes. The supernatant was kept at 4° C. The supernatant was diluted 1:8 (v/v) into 100 mM Tris, 5 mM ZnCl$_2$, pH 7.2. The suspension was centrifuged at 12000 g for 10 minutes. The supernatant was discarded. The pellet was resuspended in 200 ml of 100 mM Tris, 8 M Urea, pH 7.2. The suspension was centrifuged at 12000 g for 30 minutes. The supernatant was discarded. The washing procedure was repeated two more times. Resolubilization was achieved by suspension of the washed pellet in 200 mL of 100 mM Tris, 6 M Guanidine hydrochloride, 10 mM DTT, pH 7.2. The suspension was centrifuged at 12000 g for 30 minutes. The protein concentration in the supernatant as measured by HPLC protein assay was 10 mg/mL. The IL-21 sample was then stored at 4° C.

2. The solubilization of IL-21 was achieved by suspending the washed inclusion body body pellet in 6 M Guanidine hydrochloride, 40 mM dithiothreitol (DTT) prepared in 100 Mm Tris, pH 8.0 (GDT40). Approximately 150 ml of GDT40 was used per liter of original fermentation broth. The solubilization took place at room temperature for one hour. The suspension was then centrifuged. The supernatant from dissolved inclusion bodies was refolded by dilution (20-30x) into a refolding buffer containing a 0.75 M arginine plus DTT/cystine oxidation-reduction pair. Refolding was allowed to take place for 5-16 hours after which the pH of the mixture was adjusted to pH 5.5 and filtered prior to delivery to purification.

D. Direct Disruption of Harvested Broth from ZGOLD1

The harvested E. coli ZGOLD1 broth was produced by fed-batch fermentation in PCOL22 medium (described above), and contained approximately 9-10 g/L of IL-21met in inclusion body form. The fermentation broth (0.5 L) was diluted to 1.0 L with dionized water and passed through the APV homogenizer three times at 10,000 psi. The broth was then centrifuged at 15,000×g for 30 minutes. The supernatant was discarded, taking care to retain the loose pellet. The pellet was resuspended in 500 ml of DI water and centrifuged at 15,000×g for 30 minutes. The supernatant was discarded, taking care to retain the loose pellet. The pellet was resuspended in 500 ml of DI water and centrifuged at 15,000×g for 30 minutes. The supernatant was discarded, taking care to retain the loose pellet. The inclusion body pellet was stored at −80° C. or refolded without freezing.

Example 10

A. Solubilization of Washed Inclusion bodies

Solubilization was achieved by suspension of the washed inclusion body pellet in 150 mL of 100 mM Tris, 6 M Guanidine hydrochloride, 20 mM dithiothreitol, pH 7.5 at room temperature for one hour. The suspension was then centrifuged at 12000 g for 30 minutes. The protein concentration in the supernatant as measured by HPLC protein assay was 21 mg/mL. The IL-21 sample was then stored at 4° C.

B. Solubilization of Washed Inclusion bodies from ZGOLD1

Solubilization was achieved by suspension of a washed inclusion body pellet from 1 liter of fermentation broth in 150 mL of 100 mM Tris, 6 M Guanidine hydrochloride, 40 mM dithiothreitol, pH 8.0 at room temperature for one hour. The suspension was then centrifuged at 15,000×g for 30 minutes. The protein concentration in the supernatant as measured by HPLC protein assay was 29 mg/mL. The IL21 sample was then stored at 4° C.

C. Clarification of Solubilized Inclusion Bodies

Immobilized metal affinity chromatography (IMAC) resin was used to clarify solubilized 11-21 inclusion body pellets. In one example, washed inclusion body pellets were solubilized for 1 hour at room temperature in 6M guanidine HCl containing 10 mM Imidazole, pH 7.5, 1.0 ml His-trap columns (Amersham Biosciences) were charged with 0.5 ml of 0.1M NiSO4. After charging and water washing, 5.0 ml of binding buffer consisting of 6M GuHCl, 20 mM Imidazole, 0.5M NaCl, and 20 mM phosphate was used to equilibrate the column.

The solute sample (1.0 ml) was applied to the column, and the column was washed with 5.0 ml of the binding buffer. IL-21 was eluted by applying 2.5 ml of elution buffer (6M GuHCl, 0.5M Imidazole, 0.5M NaCl, and 20 mM phosphate) to the column. The elution step was repeated, and the samples were analyzed for purity and clarification using SDS-Page gels.

Example 11

Refolding

A. Renaturation with GSH and GSSG

The concentration of IL-21 in the solubilized fraction was determined by reverse phase HPLC to be 21 mg/ml. Determination of the refolding buffer volume was based on the amount of solute and the concentration of IL-21 present in the solute. The refolding buffer (50 mM Tris, 10 mM NaCl, 0.5 mM KCl, 2 mM $MgCl_2$, 2 mM $CaCl_2$, 0.05% (w/v) PEG3350, 1.1 M L-Arginine, 2 mM GSH, 1 mM GSSG, pH 7.5) was chilled to room temperature (21° C.). GSH and GSSG were dissolved immediately before use.

The solute containing IL-21 (175 ml) was added slowly (1.5 hours) to the refolding buffer (11 L) with mixing. IL-21 was added to the refolding mixture to a final concentration of 0.30 mg/ml. The temperature range was between 20-22° C. The vessel containing the refold mixture was left open to the atmosphere. Refolding was allowed to take place for 16 hours. The concentration of refolded IL-21 was determined to be 0.165 mg/ml, which represents a 55% renaturation yield.

B. Renaturation with DTT and GSSG

The concentration of IL-21 in the solubilized fraction was determined by reverse phase HPLC to be 15.02 mg/ml. Determination of the refolding buffer volume was based on the amount of solute and the concentration of IL-21 present in the solute. The refolding buffer (50 mM Tris, 10 mM NaCl, 0.5 mM KCl, 2 mM $MgCl_2$, 2 mM $CaCl_2$, 0.05% (w/v) PEG3350, 1.1 M L-Arginine, 2 mM DTT, 4 mM GSSG, pH 7.5) was chilled to room temperature (21° C.). DTT and GSSG were dissolved immediately before use.

The solute containing IL-21 (88 ml) was added slowly (1.0 hours) to the refolding buffer (1.0 L) with mixing. IL-21 was added to the refolding mixture to a final concentration of 0.50 mg/ml. The temperature range was between 20-22° C. The vessel containing the refold mixture was left open to the atmosphere. Refolding was allowed to take place for 16 hours. The concentration of refolded IL-21 was determined to be 0.27 mg/ml, which represents a 59.5% renaturation yield.

C. Renaturation with Cysteine and Cystine Dihydrochloride

The concentration of IL21 in the solubilized fraction was determined by reverse phase HPLC to be 18.6 mg/ml. Determination of the refolding buffer volume was based on the amount of solute and the concentration of IL-21 present in the solute. The refolding buffer (50 mM Tris, 10 mM NaCl, 0.5 mM KCl, 2 mM $MgCl_2$, 2 mM $CaCl_2$, 0.05% (w/v) PEG3350, 1.0 M L-Arginine, 4 mM cysteine, 2 mM cystine HCl, pH 7.5) was chilled to room temperature (21° C.). Cysteine and cystine dihydrochloride were dissolved immediately before use.

The solute containing IL-21 (20.5 ml) was added slowly (0.5 hours) to the refolding buffer (0.78 L) with mixing. IL-21 was added to the refolding mixture to a final concentration of 0.49 mg/ml. The temperature range was between 20-22° C. The vessel containing the refold mixture was left open to the atmosphere. Refolding was allowed to take place for 21 hours. The concentration of refolded IL-21 was determined to be 0.29 mg/ml, which represents a 58% renaturation yield.

D. Renaturation with DTT and Cystine Dihydrochloride

The concentration of IL-21 in the solubilized fraction was determined by reverse phase HPLC to be 18.6 mg/ml. Determination of the refolding buffer volume was based on the amount of solute and the concentration of IL-21 present in the solute. The refolding buffer (50 mM Tris, 10 mM NaCl, 0.5 mM KCl, 2 mM $MgCl_2$, 2 mM $CaCl_2$, 0.05% (w/v) PEG3350, 1.1 M L-Arginine, 2 mM DTT, 4 mM cystine dihydrochloride, pH 7.5) was chilled to room temperature (21° C.). DTT and GSSG were dissolved immediately before use.

The solute containing IL-21 (20.5 ml) was added slowly (0.5 hours) to the refolding buffer (0.78 L) with mixing. IL-21 was added to the refolding mixture to a final concentration of 0.49 mg/ml. The temperature range was between 20-22° C. The vessel containing the refold mixture was left open to the atmosphere. Refolding was allowed to take place for 16 hours. The concentration of refolded IL-21 was determined to be 0.28 mg/ml, which represents a 58% renaturation yield.

E. Time-Pulse Refolding

Time-pulsed refolding provides a method for refolding human IL-21met to a final concentration of 0.3-0.9 mg/mL. In the batch refolding, the final IL-21 protein concentration in the refolding buffer was optimized between 0.2-0.3 mg/ml. A high concentration of arginine (1 M) was required, and the yield of the refolding step was 40% to 50%. While satisfactory by conventional criteria of protein refolding, it would be highly desirable to refold IL-21met at even higher concentration.

The preparation of solubilized inclusion bodies was as described in Example 4 with the exception of final protein concentration being 15 mg/ml. A 1:50 dilution of the solute was achieved using refolding buffer as described. The solution was then stirred for 3 hours at room temperature. A sample was taken at the end of the 3 hours period and centrifuged. The supernatant was subjected to HPLC analysis. The process was then repeated four more times.

The percent yield of properly refolded IL-21met remained constant during the first three repeats, but dropped after the fourth repeat. The highest final protein concentration achieved without sacrifice in yield was 0.9 mg/ml. High protein concentration (>0.3 mg/ml) during the early stage of refolding (<3 hours) resulted in lower yield due to aggregation. Once the refolding was completed (>3 hours), addition of refolding stock can be commenced without sacrifice in yield. The maximum guanidine hydrochloride concentration in the final refolding buffer was 0.3 to 0.6 M.

F. Refolding with DTT and Cystine in Decreased Arginine Concentrations

The concentration of the IL21 in the solubilized fraction was determined by reverse phase HPLC to be 14.53 mg/ml. The refolding buffer (50 mM Tris, 10 mM NaCl, 0.5 mM KCl, 2 mM $MgCl_2$, 2 mM $CaCl_2$, 0.05% (w/v) PEG3350, 0.75 M L-Arginine, 2 mM DTT, 4 mM cystine, pH 8.0) was chilled to 21° C. Cystine was dissolved into 0.25 M NaOH to a concentration of 80 mM and added along with DTT immediately before use.

The solute containing IL21 (96 ml) was added slowly (1.0 hours) to the refolding buffer (1.0 L) with mixing. The IL21 was added to the refolding mixture to a final concentration of 0.61 mg/ml. The temperature range was between 14-16° C. The vessel containing the refold mixture was left open to the atmosphere. Refolding was allowed to take place for 16 hours. The refolded IL21 was determined to be 0.40 mg/ml, and represents a 66% re-naturation yield.

G. Volumetric Refolding with DTT and Cystine

Volumetric refolding is based on the volume of the IL21 solute and not on the concentration of IL21 in the solute. The concentration of the IL21 in the solubilized fraction was determined by reverse phase HPLC to be 26.1 mg/ml. The refolding buffer (50 mM Tris, 10 mM NaCl, 0.5 mM KCl, 2 mM $MgCl_2$, 2 mM $CaCl_2$, 0.05% (w/v) PEG3350, 0.75 M L-Arginine, 2 mM DTT, 4 mM cystine, pH 8.0 was chilled 15° C. Cystine was dissolved into 0.25 M NaOH to a concentration of 80 mM and added along with DTT immediately before use.

The solute containing IL21 (935 ml) was added slowly (2.0 hours) to the refolding buffer (28.0 L) with mixing. The IL21 was added to the refolding mixture to a final concentration of 0.83 mg/ml. The temperature range was between 14-16° C. The vessel containing the refold mixture was left open to the atmosphere. The refolding was allowed to take place for 16 hours. The refolded IL21 was determined to be 0.51 mg/ml, and represents a 61% renaturation yield.

H. Volumetric Refolding WIB's from ZGOLD1

The concentration of the IL21 in the solubilized fraction was determined by reverse phase HPLC to be 29.9 mg/ml. The refolding buffer (50 mM Tris, 10 mM NaCl, 0.5 mM KCl, 2 mM $MgCl_2$, 2 mM $CaCl_2$, 0.05% (w/v) PEG3350, 0.75 M L-Arginine, 2 mM DTT, 4 mM cystine, pH 8.0 was chilled 15° C. Cystine was dissolved into 0.25 M NaOH to a concentration of 80 mM and added along with DTT immediately before use.

The solute containing IL21 (935 ml) was added slowly (2.0 hours) to the refolding buffer (27.3 L) with mixing. The IL21 was added to the refolding mixture to a final concentration of 0.96 mg/ml. The temperature range was between 14-16° C. The vessel containing the refold mixture was left open to the atmosphere. The refolding was allowed to take place for 16 hours. The refolded IL21 was determined to be 0.60 mg/ml, and represents a 62.3% renaturation yield.

Example 12

A. Clarification of Refolded IL-21

This step is to stop the refolding reaction and to remove particulates from the refolded IL-21 solution. Refolded IL-21 is typically adjusted to pH 5.5 and then passed through a 1.2 μm nominal filter. In some cases the pH is not adjusted prior to the filtration, and in other cases a different size (0.45-2.0 μm) or type of filter could be used. It is possible to remove the particulates by centrifugation, using a Carr powerfuge continuous centrifuge (Carr Separations, Inc., Franklin, Mass.) or by centrifugation in bottles.

After refolding, the conductivity of the buffer solution needs to be reduced for loading onto the SP550 C capture resin. The cloudy solution also needs to be filtered to remove unfolded IL21 and precipitated *E. coli* proteins. In one example, 29.5 L of refolded buffer containing refolded IL-21 was diluted with 1.4 parts (42.0 L) of 25 mM acetate buffer pH 5.5. The solution was allowed to precipitate at room temperature for 4 hours. The solution was then filtered through a 1.2-0.8 um Cuno Zeta Plus depth filter.

B. Dilution and Clarification of Refolded IL-21

This step is to stop the refolding reaction, dilute the refolded material to enable binding to cation exchange chromatography, and to remove particulates from the refolded IL-21 solution. Refolded IL-21 is typically adjusted to pH 5.5, and then diluted 1.4 fold with 25 mM sodium acetate, pH 5.5. This solution is allowed to settle for approximately four hours at room temperature with a view to enhance physical separation of soluble and insoluble proteins present in the diluted refold solution. The settled and diluted refold solution mostly devoid of particulates is then typically passed through a 1.2 to 0.8 μm depth filter (Cuno Zeta Plus A30M03).

Example 13

Concentration of Clarified, Refolded IL-21

Clarified, refolded IL-21 is concentrated 10-fold to 30-fold by tangential flow filtration. The tangential flow filtration apparatus and membranes (Millipore Pellicon Biomax 5 kDa molecular weight cut-off plate(Millipore, Bedford, Mass.) and frame system or Amersham Biosciences 10 kDa molecular weight cut-off hollow fiber system) are sanitized using 0.5 M NaOH and rinsed with water. For refolded IL-21 from 1 L of fermentation broth, 0.2 $m^2$ to 0.3 $m^2$ of membrane area is used with a cross-flow rate of approximately 48 L/hr and a transmembrane pressure of 20 psi to 30 psi.

Example 14

Capture of Refolded IL-21

A. Cation Exchange Using TOYOPEARL SP 550 C Resin

Following concentration, IL-21 is captured on a cation exchange column. In one example, the concentrated IL-21 is diluted 3-fold with water or 25 mM sodium acetate, pH 5.5. A precipitate is formed which is removed by filtration after 30 minutes incubation at room temperature. A Millipore 1.2 μm Polysep II filter (Millipore) or a 1.2-0.8 μm Cuno Zeta Plus A30MO3 membrane (Cuno, Meriden, Conn.) is used. The filtered IL-21 is loaded onto a column of TOYOPEARL_SP550C resin (Tosoh Biosep) equilibrated to equilibration buffer (25 mM sodium acetate, 0.2 M NaCl, pH 5.5). The column is loaded at a capacity of 6-10 g IL-21 per L resin, the bed height is 15 cm, UV absorbance at 280 nm and 215 nm is monitored, and a flow rate of 150 cm/hr is used. Following loading the column is washed with equilibration buffer until the UV absorbance returns to baseline. The column is then washed with 4 column volumes of 50% equilibration buffer, 50% elution buffer (25 mM sodium acetate, 1.0 M NaCl, pH 5.5). IL-21 is eluted from the column with 25% equilibration buffer, 75% elution buffer. Alternatively, following loading of IL-21 onto the column and washing with equilibration buffer, IL-21 is eluted from the column with a 10 column volume linear gradient from 100% equilibration buffer to 100% elution buffer.

Alternatively, following pH adjustment, dilution, hold step, and filtration using depth filtration, the IL-21 is captured on cation exchange chromatography. The filtered solution is loaded onto a column of TOYOPEARL SP 550 C resin (Tosoh Biosep) and equilibrated to equilibration buffer conditions (25 mM sodium acetate, pH 5.5, 0.4 M NaCl). The column is loaded at a capacity of 6 to 15 g IL-21 per L resin. UV absorbance at 280 nm and 215 nm is monitored, and a flow rate of 150 cm/hr is used. Following loading, the column is washed with equilibration buffer until the UV absorbance returns to baseline. IL-21 is eluted from the column using a step gradient to 100% elution buffer (25 mM sodium acetate, pH 5.5, 0.75 M NaCl).

B. Cation Exchange Chromatography Using SP Sepharose XL Resin

The concentrated IL-21 is diluted 10-fold with 25 mM sodium acetate, pH 5.5. A precipitate is formed which is removed by filtration after 30 minutes incubation at room temperature. A Millipore 1.2 μm Polypro XL filter (Millpore) is followed by a 0.45 μm Whatman Polycap 75 AS filter (Maidstone, Kent, UK). The filtered IL-21 is loaded onto a column of Amersham Biosciences SP Sepharose XL resin equilibrated to equilibration buffer (25 mM sodium acetate, 0.2 M NaCl, pH 5.5). The column is loaded at a capacity of 3-6 g IL-21 per L resin, the bed height is 15 cm, UV absorbance at 280 nm and 215 nm is monitored, and a flow rate of 150 cm/hr is used. Following loading the column is washed with equilibration buffer until the UV absorbance returns to baseline. The column is then washed with 4 column volumes of 25% equilibration buffer, 75% elution buffer (25 mM sodium acetate, 1.0 M NaCl, pH 5.5). IL-21 is eluted from the column with 50% equilibration buffer, 50% elution buffer.

C. Cation Exchange Chromatography using Streamline SP XL Resin

In another example, IL-21 is not concentrated by tangential flow filtration prior to capture by cation exchange chromatography. Following refolding, the pH is adjusted to 5.5 and the material is filtered through a 1.2 μm nominal cut off filter. An Amersham Biosciences Streamline column packed with Amersham Biosciences Streamline SP XL is equilibrated to equilibration buffer (25 mM sodium acetate, 0.2 M NaCl, pH 5.5). Following equilibration, the filtered, pH-adjusted, refolded IL-21 is loaded onto the column using in-line dilution, i.e. 30% filtered, pH-adjusted, refolded IL-21 and 70% water is loaded using the chromatography system to generate the correct ratio. The IL-21 is loaded onto the column in an upflow direction using a flow rate that causes a 2-fold expansion of the resin compared to the settled bed height. Once the filtered, pH-adjusted refolded IL-21 has been loaded it is replaced with equilibration buffer. Pumping onto the column is then continued with 30% equilibration buffer and 70% water until the conductivity recorded at the column inlet is <10 mS/cm. The column is then washed with equilibration buffer in upflow mode with a 2-fold settled bed height expansion until the UV absorbance at 280 nm returns to baseline. The flow is then stopped and the resin bed allowed to settle. The plunger of the Streamline column is lowered to the settled bed height and the column is washed with equilibration buffer in downflow mode for 2 column volumes at a flow rate of 150 cm/hr. IL-21 is then eluted with 50% elution buffer (25 mM sodium acetate, 1.0 M NaCl, pH 5.5) and 50% equilibration buffer in downflow mode at 150 cm/hr.

Example 15

Intermediate Purification of IL-21 by Hydrophobic Interaction Chromatography

A. Hydrophobic Interaction Chromatography (HIC) Using butyl Sepharose Resin

Il-21 is adjusted to 1.5 M ammonium sulfate by adding 198 gr solid ammonium sulfate per liter IL-21 solution. The solution is stirred until the ammonium sulfate is dissolved and then solid material is removed by filtration through a 0.45 μm nominal cut-off filter. In one example a 15 cm high column of Amersham Biosciences butyl Sepharose 4 FF is equilibrated to equilibration buffer (25 mM sodium acetate, 50 mM sodium chloride, 1.5 M ammonium sulfate, pH 5.5). The adjusted, filtered IL-21 solution is loaded onto the column at a capacity of 1.0-2.5 g IL-21 per L resin at a flow rate of 150 cm/hr. UV absorbance at 280 nm and 215 nm is monitored. Following loading the column is washed with equilibration buffer until the UV absorbance returns to baseline. IL-21 is eluted from the column with 50% equilibration buffer and 50% elution buffer (25 mM sodium acetate, 50 mM sodium chloride, pH 5.5). Alternatively, following loading of IL-21 onto the column and washing with equilibration buffer, IL-21 is eluted from the column with a 10 column volume linear gradient from 100% equilibration buffer to 100% elution buffer.

B. HIC Using TOYOPEARL 650M Resin

In another example a different resin, Tosoh Biosep TOYOPEARL butyl 650M, is used to purify the IL-21. The method is the same as that used for the butyl Sepharose FF resin with the following exceptions: the cation exchange eluate is adjusted to 1.5 M $(NH_4)_2SO_4$ using a 3.5 M $(NH_4)_2SO_4$ stock solution; the adjusted, filtered IL-21 solution is loaded onto the column at a capacity of 10-12 g IL-21 per L resin; following loading, the column is washed with equilibration buffer until UV absorbance returns to baseline; IL-21 is eluted from the column with 100% elution buffer (25 mM sodium acetate, pH 5.5, 0.05 M NaCl, 0.15 M $(NH_4)_2SO_4$).

Example 16

A. Concentration and Buffer Exchange of Purified IL-21 to Phosphate Buffered Saline Following purification IL-21 is subject to ultrafiltration and diafiltration to concentrate it and exchange it to a buffer suitable for storage. A tangential flow filtration apparatus and membranes (Millipore Pellicon Biomax 5 kDa molecular weight cut-off plate and frame system) are sanitized using 0.5 M NaOH and rinsed with water. For purified IL-21 from 1 L of fermentation broth, 0.1 $m^2$ or less of membrane area is used with a cross-flow rate of approximately 20-25 L/hr and a transmembrane pressure of 10 psi to 15 psi. IL-21 is concentrated to approximately 15-20 mg/mL and then diafiltered against approximately 5-10 diavolumes of phosphate buffered saline, pH 6.0. The concentrated, buffer exchanged IL-21 is stored at −80° C.

B. Concentration and Buffer Exchange of Purified IL-21 to Histidine/Mannitol Buffer Following purification by SP HP Sepharose, IL-21 is subject to ultrafiltration and diafiltration to concentrate and exchange purified IL-21 into a buffer suitable for storage. A tangential flow filtration apparatus and membranes (Millipore Pellicon Biomax 5 kDa molecular weight cut-off plate and frame system) are sanitized using 0.5 M NaOH and rinsed with water. For purified IL-21, from 1 L of fermentation broth, 0.1 $m^2$ or less of membrane area is used with a cross-flow rate of approximately 30 L/hour at a transmembrane pressure of 25. IL-21 is concentrated to approximately 10-15 mg/ml, and then diafiltered against approximately 5-10 diavolumes of 10 mM histidine, 4.72% (w/v) mannitol, pH 5.0-5.3. The resulting solution is sterile filtered.

Example 17

Additional Purification of IL-21

A. Cation Exchange Chromatography Using SP HP Sepharose Resin for Polishing

Further purification using SP HP Sepharose is performed to further improve overall purity. The TOYOPEARL butyl 650M elutate is diluted to 30 mS/cm with water, and then adjusted to pH 6.0 using a dibasic sodium phosphate stock solution. The adjusted solution is then filtered using a 0.22 μm filter. The filtered material is loaded onto the column at 10-15 g IL-21 per L resin on a column equilibrated with 50 mM phosphate, pH 6.0, 0.3 M NaCl. UV 280 nm and UV 215 nm are used to monitor the chromatography. After loading, the column is washed with equilibration buffer until UV reaches baseline. IL-21 is eluted from the column using a 20-column volume gradient to 100% elution buffer (50 mM phosphate, pH 6.0, 0.7 M NaCl).

B. Anion Exchange Chromatography

L-21 is passed through an anion exchange column to remove endotoxin. A column of Amersham Biosciences Q Sepharose FF is equilibrated with equilibration buffer (20 mM Tris, pH 8.0). The IL-21 solution is adjusted to a conductivity of <10 mS/cm with equilibration buffer. The adjusted IL-21 solution is loaded onto the column at a flow rate of 150 cm/hr. IL-21 does not bind to the column and is collected in the flow-through. In other examples, Amersham Biosciences DEAE Sepharose FF resin or Pall Mustang Q membranes can be used instead of Q Sepharose FF to purify IL-21. In still other examples, pH values in the range from 5.0 to 9.0 have been shown to result in IL-21 passing through anion exchange media.

C. Hydrophobic Interaction Chromatography

In other examples, hydrophobic interaction chromatography, using conditions different than those described above with butyl resin, has been used to purify IL-21. Amersham Biosciences phenyl Sepharose FF high sub, Amersham Biosciences Phenyl Sepharose HP and Amersham Biosciences butyl Sepharose 4 FF can be used as resin in both binding and flow through modes. To bind IL-21, the columns are equilibrated to 25 mM sodium acetate, 50 mM sodium chloride, 1.5 M ammonium sulfate, pH 5.5. IL-21 is adjusted to 1.5 M ammonium sulfate by adding solid ammonium sulfate and stirring until it is dissolved. The adjusted IL-21 solution is loaded onto the equilibrated column at a flow rate of 150 cm/hr. UV absorbance at 280 nm and 215 nm is monitored. Following washing, the IL-21 is eluted from the column with a 10 column volume linear gradient from 100% equilibration buffer to 100% elution buffer (25 mM sodium acetate, 50 mM NaCl, pH 5.5). In flow through mode the IL-21 containing solution is adjusted to 1.0 M or less ammonium sulfate, and loaded onto a column equilibrated with 25 mM sodium acetate, 50 mM NaCl, 1.0 M ammonium sulfate, pH 5.5. The flow through is collected.

In other examples, hydrophobic interaction chromatography using sodium sulfate as salt, rather than ammonium sulfate, has been used to purify IL-21. Amersham Biosciences phenyl Sepharose FF high sub, Amershan Biosciences Phenyl Sepharose HP and Amersham Biosciences butyl Sepharose 4 FF can be used as resin. The columns are equilibrated to 25 mM sodium acetate, 50 mM sodium chloride, 1.5 M sodium sulfate, pH 5.5. Il-21 is adjusted to 1.5 M sodium sulfate by adding solid sodium sulfate and stirring until the sodium sulfate is dissolved. The adjusted IL-21 solution is loaded onto the equilibrated column at a flow rate of 150 cm/hr. UV absorbance at 280 nm and 215 nm is monitored. Following washing, the IL-21 is eluted from the column with a 10 column volume linear gradient from 100% equilibration buffer to 100% elution buffer (25 mM sodium acetate, 50 mM NaCl, pH 5.5).

In another example, HIC FPLC flow-through was performed on a BIOCAD 700E FPLC system (Perseptive Biosystems, Framingham, Mass.) equipped with Butyl Sepharose 4 FF column (Amersham Biosciences). The column was conditioned with 25 mM NaOAc, 600 mM NaCl, 1 M $(NH_4)_2SO_4$. pH 5.5. Solid $(NH_4)_2SO_4$ was added to the cation-exchange eluate to a final concentration of 1M. The solution was loaded onto the column and IL-21 was collected in the flow-through.

D. IMAC Using Metal Chelating Sepharose

Amersham Biosciences Chelating Sepharose (Amersham) is used to further purify IL-21. Captured IL-21 CIE eluate is loaded onto a column charged with copper, zinc, or nickel ions then equilibrated with 25 mM sodium acetate, pH 5.5; 0.8 M NaCl. UV 280 nm and UV 215 nm are used to monitor the chromatography. The column is then washed with equilibration buffer to baseline, and eluted using a 10 CV gradient to 100% elution buffer (25 mM sodium acetate, pH 5.5; 0.8 M NaCl, 0.5 M imidizole).

Example 18

A. Reversed Phase HPLC Analysis of Solubilized IL-21 in Acetonitrile Buffer The method described here is used to quantify IL-21 in solubilized inclusion body samples and purified samples. A 4.6×50 mm Jupiter C5 column (300 Å, 5 µm, Phenomenex) is used on an Agilent Technologies 1100 series HPLC system with thermostated autosampler and thermostatted column compartment. A 0.2 µm pre-column filter is placed before the column. Mobile phase A is 0.1% TFA in HPLC grade water and mobile phase B is 0.1% TFA in acetonitrile.

The elution gradient/time table for purified samples is as follows:

TABLE 10

| Time | % B |
|---|---|
| 0 | 5 |
| 3.5 | 5 |
| 4 | 41 |
| 14 | 48 |
| 14.5 | 95 |
| 17 | 95 |
| 17.5 | 5 |
| 20 | 5 |

The elution gradient/time table for solubilized inclusion body samples is:

TABLE 11

| Time | % B |
|---|---|
| 0 | 5 |
| 4.0 | 5 |
| 5.5 | 40 |
| 20.0 | 50 |
| 21.0 | 95 |
| 22.0 | 95 |
| 23.0 | 5 |
| 30.0 | 5 |

The column is equilibrated to the initial conditions of the elution gradient/time table until a stable baseline is achieved.

Method parameters are as follows:
1. Flow rate: 1 ml/min.
2. Total run time: 20 minutes
3. Column temperature: 40° C.
4. Autosampler temperature: 8° C.
5. Maximum column pressure: 240 bar
6. Injector draw speed: 100 µL/minute
7. Injector eject speed: 100 µL/minute
8. Diode array detector data collection wavelength: Signal A: 280 nm, 25 nm bandwidth
9. Diode array detector data monitoring wavelength: Signal B: 215 nm, 10 nm bandwidth
10. Diode array detector data reference wavelength: Signal A: 350 nm, 25 nm bandwidth; Signal B: 350 nm, 25 nm bandwidth
11. Diode Array Detector autobalance: Prerun/Postrun mode
12. Peak width response time:>0.1 min.
13. Slit width: 4 nm
14. Needle wash function: programmed to reduce the build-up of guanidine on the needle and needle seat.

For quantitation of unfolded IL-21, IL-21 reference standard is diluted to 0.5 mg/mL with 50 mM Tris, pH 7.5, 6 M guanidine HCl, 10 mM DTT and heated at 40° C. for 20 minutes. Diluted reference standard is injected onto the column at least five levels between 10 µg and 50 µg (for example, 10, 20, 30, 40 and 50 µg injections). Solubilized IL-21 samples are spun in a microfuge and diluted 1:10 in 50 mM Tris, pH 7.5, 6 M guanidine HCl prior to injection of 25 µl of sample.

For quantitation of folded IL-21, IL-21 reference standard is diluted to 1.0 mg/ml with phosphate buffered saline, pH 6.0. Folded IL-21 samples are injected to the HPLC without any treatment. Following chromatography the area under the IL-21 peaks is integrated. A standard curve is constructed and the concentration of IL-21 in the samples is read off the standard curve.

B. Methanol-Based RP-HPLC for Quantitation of IL-21

A fifteen-minute methanol-based RP-HPLC method may also be used to evaluate IL-21 preparations ranging from solubilized inclusion bodies through final product.

Method Parameters for IL-21 Methanol-based RP-HPLC Analysis are as follows:

Column: Zorbax 300SB-CN (4.6×50 mm), 3.5 micron
Mobile Phase A: 0.154% TFA, HPLC grade Water
Mobile Phase B: 0.154% TFA, Methanol
Elution Gradient/Time Table

TABLE 12

| Time | % B | Flow Rate (mL/minute) |
|---|---|---|
| 0 | 50 | 1.0 |
| 1.0 | 50 | 1.0 |
| 11.0 | 100 | 1.0 |
| 12.0 | 100 | 1.0 |
| 12.5 | 50 | 1.5 |
| 15.0 | 50 | 1.5 |

Total Run-Time: 15 minutes
Column Temperature: 40° C.
Autosampler Temperature: 5° C.
Injector Draw Speed: 90 µL/minute
Injector Eject Speed: 90 µL/minute
DAD Monitoring Wavelength: Signal A: 280 nm, 8 nm bandwidth
Signal B: 215 nm, 8 nm bandwidth
Signal C: 280 nm, 6 nm bandwidth (Reference Wavelength OFF)
DAD Data Collection Wavelength: Signal A: 280 nm, 8 nm bandwidth
DAD Reference Wavelengths: Signals A and B, 360 nm, 16 nm bandwidth
DAD Autobalance: Prerun/Postrun mode
Peak Width Response Time: >0.1 min.
Slit Width: 4 nm
Margin for Negative Absorbance: 100 mAu
Standard Curve Load Amount Range: 1-20 µg
Minimal Injection Volume: 5 µL

Example 19

OmpT Deficient Strain for Expressing IL-21

A. Construction of a New Host Strain for Production of IL-21

The current process for production of IL-21 includes expression in the *E. coli* host W3110 [F-mcrA mcrb IN(rmD-rmD)1λ-]. While W3110 is a robust host for production of IL-21, it is not ideal for downstream processing. Upon cell lysis, IL-21 is cleaved at lysine 74 (as shown in SEQ ID NO:28) by the OmpT protease present in the outer membrane. This protease is known to cleave other heterologous recombinant proteins, including FGF-18. Proteolysis of IL-21 does not occur in strains lacking OmpT, such as BL21 [F-ompT hsdSB (rB-mB-) gal dcm lon]. While OmpT activity can be minimized during cell lysis with the addition of $ZnSO_4$ or $CUSO_4$, the purification scheme had to be designed to remove truncated IL-21 from the final product. In an effort to streamline the process for production of IL-21, the OmpT protease was removed from W3110 to create a new production strain. The construction of this new *E. coli* host strain is described below.

B. Construction of Plasmid pCHAN1 for Expression of the Red Recombinase Operon

A strategy based on homologous recombination was used to remove the OmpT protease from W3110. In order to delete genes efficiently from the *E. coli* chromosome by homologous recombination, certain enzymes with recombinase activity must be present within the cells. To accomplish this, a plasmid was constructed harboring the Red recombinase operon from bacteriophage λ. A fragment containing the Red recombinase genes was synthesized from bacteriophage λ DNA (New England Biolab) by PCR using recombination-specific primers ZC43,586 (SEQ ID NO:29) and ZC43,587 (SEQ ID NO:30) The reaction contained 100 pmol each of primers ZC43,586 and ZC43,587, 10 μl of 10×PCR buffer (Boehringer Mannheim), 1 μl Pwo Polymerase (Boehringer Mannheim), 10 μl of 0.25 mM nucleotide triphosphate mix (Perkin Elmer), and $dH_2O$ in a final volume of 100 μl. The PCR reaction consisted of a single 5 minute cycle at 94° C., followed by 30 cycles of 1 minute at 94° C., 1 minute at 50° C. and 1 minute at 72° C. The last of the 30 cycles was followed by a 5-minute extension at 72° C. and the reaction concluded with an overnight hold at 4° C. The resulting 1964 base pair (bp) fragment contained the Red recombinase operon (SEQ ID NO: 31). The nucleotide sequence as shown in SEQ ID NO:31 encodes for three genes, Gam(γ) as shown from nucleotides 41-454, Bet(β) as shown from nucleotides 463-1245, and Exo as shown from nucleotides 1245-1922.

The Red recombinase operon was incorporated into a plasmid by homologous recombination in yeast. Competent yeast cells (100 μl of *S. cerevisiae* SF838-9Dα) were combined with 100 ng of SmaI-digested pTAP399 (deposited at American Type Culture Collection in Manassas, Va. (undesignated at filing time)), acceptor vector and 1 μg of the PCR fragment from above. The yeast/DNA mixture was transferred to a 0.2 cm electroporation cuvette and pulsed at 0.75 kV (5 kV/cm), infinite Ω, 25° F. capacitor. The transformation mixture was then added to 1 ml of 1.2 M sorbitol and incubated at 30 C for 1 hour. The cells were plated in 500 μl aliquots onto two URA DS plates (2% dextrose, 2% sorbitol) and incubated at 30° C. for 2 days. After about 48 hours the Ura+ yeast transformants from the plates were suspended in 2 ml $H_2O$ and pelleted by centrifugation. The cell pellet was resuspended in 1 ml of Qiagen PI lysis buffer (Qiagen) and transferred to a fresh tube containing 1 ml of 0.5 mm zirconia/silica beads (Biospec Products Inc.). The cells were lysed, samples were allowed to settle, 250 μl of lysate were transferred to a fresh tube, and plasmid DNA was isolated using the Qiagen Spin Miniprep kit according to the manufacturer's instructions.

Electrocompetent *E. coli* DH10B cells (Invitrogen) were transformed with 1 μl of the yeast DNA prep. The cells were pulsed in 0.1 cm cuvettes at 2.0 kV, 25° F. and 100Ω. Following electroporation, 250 μl SOC (2% Bacto Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added to each sample. Cells were allowed to recover at 37° C. for 2 hours. The entire 250 μl sample was plated in one aliquot on an LB plate (LB broth (Lennox), 1.8% Bacto Agar (Difco)) containing 25 mg/L kanamycin (Sigma). Plates were incubated at 37° C. overnight. Individual clones harboring the Red recombinase operon were identified by restriction digest to verify the presence of insert. The inserts of positive clones were subjected to sequence analysis. A plasmid containing the correct insert was designated pCHAN1.

The yeast sequence was then removed from the vector backbone of pCHAN1. 3.0 μl of plasmid DNA were incubated overnight with 24.3 μl $H_2O$, 2.7 μl buffer H (Roche) and 2.0 μl NotI (New England Biolabs) at 37° C. 5 μl of the overnight digest were mixed with 1 μl of 6×DNA sample dye (25% Ficoll Type 400 (Sigma), 0.25% Bromophenol blue (EM Science), 0.25% Xylene Cyanol (Kodak Biomedicals Inc.)), and 4 μl of this solution were run on a 1% agarose gel (EM Science) to verify complete digestion. To recircularize the plasmid, 14 μl of the overnight NotI digest was mixed with 4 μl of 5× ligation buffer (Invitrogen) and 2 μl ligase (Invitrogen). The ligation was incubated overnight at 25° C.

The religated pCHAN1 was transformed into W3110. Electrocompetent W3110 cells (50 μl) were transformed with 1 μl pCHAN1 DNA using the electroportation protocol for *E. coli* described above. After recovery, the entire 250 μl transformation mixture was plated in one aliquot on an LB plate containing 25 mg/L kanamycin. Plates were incubated at 37° C. overnight and ten of the resulting clones were picked for further analysis. They were grown at 37° C. overnight in 2.0 ml Superbroth II (Becton Dickinson) containing 25 μg/ml kanamycin. The following day, 1.0 ml of the overnight digest was used to confirm the presence of pCHAN1. The Qiagen Spin Miniprep Kit was used to make plasmid DNA, following the manufacturer's instructions. The identity of the plasmid was confirmed by restriction digest using EcoRI (Gibco BRL) and NotI (New England Biolabs). Isolate #3 was selected for subsequent experimentation and named EE670.

Generation of a Tetracycline Fragment for Gene Replacement in W3110

The tetracycline gene was chosen as a suitable marker for homologous recombination into the OmpT locus, rendering the OmpT gene inactive. The tetracycline promoter::tetracycline ($tet^P$::tet) fragment was generated by PCR from pBR322 DNA (New England Biolabs) using recombination-specific primers ZG45,112 (SEQ ID NO:32) and ZG45,171 (SEQ ID NO:33). The reaction mixture contained 100 pmol each of primers, ZG45,112 and ZG45,171, 10 μl of 10×PCR buffer (Boehringer Mannheim), 1 μl Pwo Polymerase (Boehringer Mannheim), 10 μl of 0.25 mM nucleotide triphosphate mix (Perkin Elmer), and $dH_2O$ in a final volume of 100 μl. The conditions for the PCR reaction were 1 cycle at 2 minutes at 94° C., followed by 30 cycles of 30 seconds at 94° C., 1

Maximum Injection Volume: 100 μL
Pressure Limit: 350 bar
Normal Running Pressure: 130-200 bar minute at 50° C. and 2 minutes at 72° C. This was followed by a 7-minute extension at 72° C. and an overnight hold at 4° C. The resulting 1590 bp fragment carries tet$^P$::tet (SEQ ID NO:34).

The PCR reaction was loaded onto a 1% agarose preparative gel to purify the tet$^P$::tet fragment. The tet$^P$::tet fragment was cut out of the gel and placed in a 0.5 ml eppendorf tube with a small hole in the bottom that was lined with aquarium filter floss (Finny Products, Inc., Cincinnati, Ohio). The tube was inserted into a 1.5 ml eppendorf tube and spun in a tabletop centrifuge at 14,000 rpm for 10 minutes at 25° C. The liquid in the bottom of the 1.5 ml tube was mixed with 10% (vol/vol) 3M NaOAc and 2 volumes of 100% Ethanol. The sample was incubated at −20° C. for 10 minutes and centrifuged for 10 minutes at 4° C. in a tabletop centrifuge to precipitate the PCR fragment. The supernatant was aspirated and the pellet resuspended in 50 µl H$_2$O. The tet$^P$::tet fragment was at a working concentration of 50 ng/µl.

The PCR fragment was ligated into the pCR4.0-BLUNT TOPO® vector (Invitrogen) to use as a positive control for the gene replacement experiments. The ligation was performed according to manufacturer's instructions. *E. coli* DH10B cells (Invitrogen) were transformed with 2 µl of the tet$^P$::tet DNA fragment using the electroporation protocol for *E. coli* described above. Following recovery, the entire 250 µl transformation mixture was plated on an LB plate containing 100 mg/L Ampicillin (Sigma). Plates were incubated at 37° C. overnight.

Ten clones were picked for further analysis. They were grown overnight in 2.0 ml Superbroth II (Becton Dickinson) containing 100 µg/ml ampicillin at 37° C. The following day, 1.0 ml of the overnight culture was used to confirm the presence of plasmid DNA. The Qiagen Spin Miniprep Kit was used to make plasmid DNA, following the manufacturer's instructions. Plasmid DNA was subjected to restriction analysis using SalI (New England Biolabs) and PstI (New England Biolabs) to verify plasmid identity and insert orientation. Isolate #1 was picked for subsequent experimentation. The plasmid was named pSDH185 and the clone, EE686.

Gene Replacement in W3110: Deletion of the OmpT Gene

A 500 ml culture of W3110/pCHAN1 was grown at 37° C. in SOB media [20 g/L tryptone, 5 g/L yeast extract, 0.5 g/L NaCl, 10 ml/L of 250 mM KCl, 5 ml/L of 2 M MgCl$_2$, pH7.0] to an OD$_{600}$ of 0.6. The culture was split into four 125 ml cultures. One culture was left as an uninduced control, while the other three were induced with 1 mM IPTG for 15 minutes, 30 minutes, or 60 minutes. At the end of their respective incubations, competent cells were made from all four cultures in the following manner. Cells were pelleted by centrifugation at 5000 rpm for 10 minutes. The supernatants were drained and each pellet was resuspended in 62.5 ml ice cold H$_2$O. The cultures were pelleted again, the supernatant was drained, and each pellet was resuspended in 31.25 ml cold 10% glycerol. The cultures were then centrifuged at 8000 rpm for 5 minutes. The pellets were drained well and resuspended in residual 10% glycerol.

All four cultures were divided into six 50 µl aliquots which were transformed in the following ways: 1) no DNA negative control, 2) 1 µl (1 µg/pl) pBR322 (New England Biolabs) positive control, 3) 11 (1 µg/1) pTAP279 positive control, 4) 1 µl pSDH185 positive control, 5) 2 µl (50 ng/1) tet$^P$::tet fragment, and 6) 4 µl (50 ng/µl) tet$^P$::tet fragment. The cells were transformed by electroporation as described above for *E. coli*. Entire transformation mixtures were plated on LB plates containing 10 mg/L tetracycline (Sigma) except for the pTAP279 controls, which were plated on LB plates containing 35 mg/L chloramphenicol (Sigma). Plates were incubated at 37° C. overnight. In addition, $10^{-6}$ and $10^{-7}$ dilutions (in H$_2$O) of each four culture were plated on LB plates to evaluate overall efficiency of the recombination process by determining the cell number.

The following day, control plates were taken out of the incubator and assessed. Samples transformed with the tet$^P$::tet fragments were allowed to incubate for an additional 24 hours prior to assay. Twenty-six of the largest clones were identified for further analysis.

Characterization of ompT Deficient Clones

Each of the 26 selected clones was grown overnight at 37° C. in 1 ml of LB with 5 µg/ml tetracycline. The following day, genomic DNA was generated from all 26 clones using the Genomic Prep DNA Isolation Kit (Amersham Pharmacia) according to the manufacturer's instructions.

The genomic DNA from each clone was diluted 1:100 in dH$_2$O to use as a template for PCR analysis. Each diluted sample was assayed using three different sets of PCR primers (three PCR reactions per clone). The reactions contained 100 pmol each of primer set #1: ZG45,357 (SEQ ID NO:35) and ZG45,350 (SEQ ID NO:36), or primer set #2: ZG45,353 (SEQ ID NO:37) and ZG45,355 (SEQ ID NO:38), or primer set #3: ZG45,354 (SEQ ID NO:39) and ZG45,359 (SEQ ID NO:40). The remainder of the 100 µl final volume was made up of 10 µl of 10×PCR buffer (Boehringer Mannheim), 1 µl Pwo Polymerase (Boehringer Mannheim), 10 µl of 0.25 mM nucleotide triphosphate mix (Perkin Elmer) and dH$_2$O. The reaction conditions were: 1 cycle for 5 minutes at 94° C., followed by 30 cycles of 30 seconds at 94° C., 1 minute at 50° C. and 2 minutes at 72° C. The PCR concluded with a 7-minute extension at 72° C. and an overnight hold at 4° C. If the OmpT gene in W3110 was successfully replaced with the tetracycline gene, primer set #1 should amplify a 1584 bp band (SEQ ID NO:41), primer set #2 should amplify an 1190 bp band (SEQ ID NO:42). The results demonstrated that 25 of the 26 clones screened were ompT$^-$. W3110 ompT$^-$ clones #1 and #3 were selected for subsequent analysis.

To confirm loss of proteolytic activity, IL-21 was incubated with cell lysates from the newly derived ompT$^-$ strains and the W3110 parent. Lysate from the ompT$^-$ strain, BL21, was included as a positive control. Cells were inoculated into Superbroth II and grown overnight at 37° C. Four 1 ml aliquots of each overnight culture were pelleted at room temperature and the cells were lysed using BugBuster® (Novagen) according to the manufacturer's instructions. Cell lysates were incubated at 25° C. for 4 hours with either: 1) 0.332 mg/ml of IL-21, or 2) 0.332 mg/ml of IL-21 in the presence of 5 mM ZnCl$_2$. Each sample was mixed with an equal volume of NuPAGE 4× Sample Buffer (Invitrogen) containing 2% β-mercaptoethanol (Sigma). The reduced samples were heated for 5 min at 100° C. and 10 µL were loaded onto a 10% NuPAGE polyacrylamide gel (Invitrogen). Electrophoresis was conducted at 130 v under denaturing conditions (SDS-PAGE) using 1× MES running buffer (Invitrogen). Gels were stained with Simply Blue Safestain (Invitrogen) following the manufacturer's instructions.

The results indicated that the OmpT protease was inactivated through gene replacement. IL-21 was completely intact after a 4-hour incubation in lysates from BL21, W3110 ompT$^-$ #1 and W3110 ompT$^-$ #3, but was completely degraded in a lysate from the W3110 parent. The activity of the OmpT protease was inhibited by zinc. In incubations containing 5 mM ZnCl$_2$ the IL-21 remained intact, supporting that OmpT was responsible for the degradation. The newly constructed W3110 ompT$^-$ strains were named ZGOLD1

(W3110 ompT⁻ #1; (deposited at American Type Culture Collection in Manassas, Va. (undesignated at filing time))) and ZGOLD3 (W3110 OmpT⁻ #3).

Characterization of ZGOLD1 and ZGOLD3

ZGOLD1 and ZGOLD3 were grown alongside the W3110 parent for assessment of growth. Cultures of all three strains were grown at 37° C. in LB to an $OD_{600}$ of 1.0. Cell density was measured hourly to assess growth. Dilutions ($10^{-6}$, $10^{-7}$ and $10^{-8}$ in $H_2O$) of each culture were plated on LB kanamycin plates (see above) to determine cell number. The results indicate that the growth of the ZGOLD strains is equivalent to that of the W3110 parent strain.

To assess transformation efficiency, cells were harvested and made competent for transformation as described above. Aliquots from each strain were transformed with either: 1) 1 μl pTAP337 (IL-21 expression plasmid; ATCC No. PA-4853), or 2) no DNA (negative control). Electroporation was carried out as described above. Following recovery, each transformation mixture was plated on an LB plate containing 25 mg/L kanamycin and incubated overnight at 37° C. The data indicate that transformation efficiency of W3110 was not affected by the removal of opmT.

Ten clones of each ZGOLD strain transformed with the IL-21 expression vector were selected to evaluate protein production. The clones were grown at 37° C. overnight in Superbroth II (containing 25 μg/ml kanamycin. The overnight cultures were used to inoculate roller drums containing Superbroth II with 25 μg/ml kanamycin. Cells were grown at 37° C. A second culture of one of the clones was grown and served as an uninduced control. When the $OD_{600}$ of each culture was 1.5-2.0, they were induced with 1 mM IPTG (ICN Biomedicals Inc.). Incubation of the cultures continued for another 5 hours. Samples of each culture were analyzed by SDS-PAGE on 4-12% gradient NuPAGE gel (Invitrogen) under reducing conditions as described above. The results indicate that IL-21 production by ZGOLD1 and ZGOLD3 is equivalent to that of the W3110 parent strain. ZGOLD1/pTAP337 #1 (deposited at American Type Culture Collection in Manassas, Va. (undesignated at filing time)) was selected for further development of the process for IL-21 production.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for producing an IL-21 protein comprising:
   (a) culturing a host cell in growth medium by fed batch fermentation, wherein the host cell is transformed with an expression vector for producing the IL-21 protein comprising the following operably linked elements:
   (i) a prokaryotic origin of replication;
   (ii) a transcriptional initiation DNA element;
   (iii) a polynucleotide sequence comprising SEQ ID NO:27; and
   (iv) a transcriptional terminator;
   (b) recovering the host cell from the growth medium; and
   (c) isolating the IL-21 protein from the host cell.

2. The method of claim 1, wherein the step (a) further comprises:
   (1) culturing the host cell in a shake flask to an OD600 of 5 to 20 in a growth medium;
   (2) inoculating a fermentation vessel with the shake flask medium containing the host cell;
   (3) culturing the host cell in a growth medium at a pH of 6.2 to 7.2, wherein a feed solution is fed into the fermentation vessel before 15 hours elapsed fermentation time (EFT);
   (4) adding an inducing agent to the fermentation vessel at 20 m 30 hours EFT; and
   (5) harvesting the host cell at 48 to 56 hours EFT.

3. The method of claim 2, wherein the host cell is *E. coli* strain W3110.

4. The method of claim 2, wherein the inducing agent is isopropyl thiogalactopyranoside (IPTG) at 0.5 to 2 mM.

5. The method of claim 2, wherein the feed solution comprises a carbohydrate selected from the group consisting of glycerol and glucose at a feed rate of 5-15 grams of carbohydrate per hour.

6. The method of claim 5, wherein the glycerol is at a concentration of 40 to 70% v/v or the glucose is at a concentration of 40 to 70% w/v.

7. The method of claim 5, wherein the glycerol is at a concentration of about 70% v/v or the glucose is at a concentration of about 60% w/v.

8. The method of claim 5, wherein the fermentation vessel is inoculated with 1 to 12% v/v of the growth medium containing the host cells.

9. The method of claim 2, wherein the feed solution comprises yeast extract.

10. A method of producing an IL-21 protein comprising:
    (a) seeding a flask with an inoculum comprising an *E. coli* W3110 host cell expressing an IL-21 polypeptide comprising SEQ ID NO:28, or an *E. coli* W3110 host cell comprising pTAP337 vector wherein the IL-21 polypeptide is expressed, and with growth medium comprising about 5 g/L glycerol;
    (b) culturing the inoculum in growth medium for 16-20 hours at about 30° C.;
    (c) transferring the cultured inoculum in growth medium to a batch fermentor at a concentration of 0.5-5% v/v inoculum;
    (d) fermenting the batch fermentation at about 37° and about pH 6.8; with about 2% glycerol;

(e) introducing a glucose feed at about 8 hours elapsed fermentation time (EFT) of about 9.5 g glucose/liter/hour and continuing until end of a fermentation run;
(f) adding IPTG at about 24 hour EFT to final concentration of 0.5 to 2 mM;
(g) fermenting about 28 hours after addition of IPTG;
(h) harvesting fermentation broth from the fermenter;
(i) adding an equal volume of water to the fermentation broth;
(j) homogenizing and centrifuging the fermentation broth to collect a cell pellet or cell slurry comprising IL-21 protein material; and
(k) isolation of the IL-21 protein from the cell pellet or cell slurry.

11. The method according to claim 10, wherein the biological activity of the IL-21 protein is measured using an IL-21 receptor-binding cell assay.

* * * * *

```
                        SEQUENCE LISTING

<160> NUMBER OF SEQ ID NOS: 42

<210> SEQ ID NO 1
<211> LENGTH: 642
<212> TYPE: DNA
<213> ORGANISM: Homo sapiens
<220> FEATURE:
<221> NAME/KEY: CDS
<222> LOCATION: (47)...(535)

<400> SEQUENCE: 1
gctgaagtga aaacgagacc aaggtctagc tctactgttg gtactt atg aga tcc         55
                                                 Met Arg Ser
                                                   1 agt cct ggc aac atg gag agg att gtc atc tgt ctg atg gtc atc ttc      103
Ser Pro Gly Asn Met Glu Arg Ile Val Ile Cys Leu Met Val Ile Phe
      5                  10                  15 ttg ggg aca ctg gtc cac aaa tca agc tcc caa ggt caa gat cgc cac      151
Leu Gly Thr Leu Val His Lys Ser Ser Ser Gln Gly Gln Asp Arg His
 20                  25                  30                  35 atg att aga atg cgt caa ctt ata gat att gtt gat cag ctg aaa aat      199
Met Ile Arg Met Arg Gln Leu Ile Asp Ile Val Asp Gln Leu Lys Asn
                 40                  45                  50 tat gtg aat gac ttg gtc cct gaa ttt ctg cca gct cca gaa gat gta      247
Tyr Val Asn Asp Leu Val Pro Glu Phe Leu Pro Ala Pro Glu Asp Val
             55                  60                  65 gag aca aac tgt gag tgg tca gct ttt tcc tgt ttt cag aag gcc caa      295
Glu Thr Asn Cys Glu Trp Ser Ala Phe Ser Cys Phe Gln Lys Ala Gln
         70                  75                  80 cta aag tca gca aat aca gga aac aat gaa agg ata atc aat gta tca      343
Leu Lys Ser Ala Asn Thr Gly Asn Asn Glu Arg Ile Ile Asn Val Ser
     85                  90                  95 att aaa aag ctg aag agg aaa cca cct tcc aca aat gca ggg aga aga      391
Ile Lys Lys Leu Lys Arg Lys Pro Pro Ser Thr Asn Ala Gly Arg Arg
100                 105                 110                 115 cag aaa cac aga cta aca tgc cct tca tgt gat tct tat gag aaa aaa      439
```

```
Gln Lys His Arg Leu Thr Cys Pro Ser Cys Asp Ser Tyr Glu Lys Lys
                120                 125                 130 cca ccc aaa gaa ttc cta gaa aga ttc aaa tca ctt ctc caa aag atg     487
Pro Pro Lys Glu Phe Leu Glu Arg Phe Lys Ser Leu Leu Gln Lys Met
            135                 140                 145 att cat cag cat ctg tcc tct aga aca cac gga agt gaa gat tcc tga     535
Ile His Gln His Leu Ser Ser Arg Thr His Gly Ser Glu Asp Ser   *
        150                 155                 160 ggatctaact tgcagttgga cactatgtta catactctaa tatagtagtg aaagtcattt   595
ctttgtattc caagtggagg agccctatta aattatataa agaaata                642

<210> SEQ ID NO 2
<211> LENGTH: 162
<212> TYPE: PRT
<213> ORGANISM: Homo sapiens

<400> SEQUENCE: 2

Met Arg Ser Ser Pro Gly Asn Met Glu Arg Ile Val Ile Cys Leu Met
 1               5                  10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 3
<211> LENGTH: 50
<212> TYPE: DNA
<213> ORGANISM: Artificial Sequence
<220> FEATURE:
<223> OTHER INFORMATION: oligonucleotide ZC29740

<400> SEQUENCE: 3
ttgacaatta atcatcggct cgtataatgt gtggaattgt gagcggataa               50

<210> SEQ ID NO 4
<211> LENGTH: 42
<212> TYPE: DNA
<213> ORGANISM: Artificial Sequence
<220> FEATURE:
<223> OTHER INFORMATION: oligonucleotide ZC29741

<400> SEQUENCE: 4
tctgatttaa tctgtatcag gctgaaaatc ttatctcatc cg                       42
```

```
<210> SEQ ID NO 5
<211> LENGTH: 62
<212> TYPE: DNA
<213> ORGANISM: Artificial Sequence
<220> FEATURE:
<223> OTHER INFORMATION: oligonucleotide ZC29736

<400> SEQUENCE: 5
gtggaattgt gagcggataa caatttcaca cagaattcat taaagaggag aaattaactc    60
cc                                                                  62

<210> SEQ ID NO 6
<211> LENGTH: 63
<212> TYPE: DNA
<213> ORGANISM: Artificial Sequence
<220> FEATURE:
<223> OTHER INFORMATION: oligonucleotide ZC29738

<400> SEQUENCE: 6
gctgaaaatc ttatctcatc cgccaaaaca cccgggagtt aatttctcct ctttaatgaa    60
ttc                                                                 63

<210> SEQ ID NO 7
<211> LENGTH: 62
<212> TYPE: DNA
<213> ORGANISM: Artificial Sequence
<220> FEATURE:
<223> OTHER INFORMATION: oligonucleotide ZC29084

<400> SEQUENCE: 7
atcaacacca acatcagcac cataaggagg agtagcatat gcaaggtcaa gatcgccaca    60
tg                                                                  62

<210> SEQ ID NO 8
<211> LENGTH: 68
<212> TYPE: DNA
<213> ORGANISM: Artificial Sequence
<220> FEATURE:
<223> OTHER INFORMATION: oligonucleotide ZC22127

<400> SEQUENCE: 8
tctgtatcag gctgaaaatc ttatctcatc cgccaaaaca tcaggaatct tcacttccgt    60
gtgttcta                                                            68

<210> SEQ ID NO 9
<211> LENGTH: 40
<212> TYPE: DNA
<213> ORGANISM: Artificial Sequence
<220> FEATURE:
<223> OTHER INFORMATION: oligonucleotide ZC22913

<400> SEQUENCE: 9
ggaaccaggt cgttcacata gttttttcagc tgatcaacaa                         40

<210> SEQ ID NO 10
<211> LENGTH: 40
<212> TYPE: DNA
<213> ORGANISM: Artificial Sequence
<220> FEATURE:
<223> OTHER INFORMATION: oligonucleotide ZC22914

<400> SEQUENCE: 10
ttgttgatca gctgaaaaac tatgtgaacg acctggttcc                          40
```

<210> SEQ ID NO 11
<211> LENGTH: 40
<212> TYPE: DNA
<213> ORGANISM: Artificial Sequence
<220> FEATURE:
<223> OTHER INFORMATION: oligonucleotide ZC22915

<400> SEQUENCE: 11
tgtttctgac gacgacctgc gttggtggac ggcggtttac                              40

<210> SEQ ID NO 12
<211> LENGTH: 40
<212> TYPE: DNA
<213> ORGANISM: Artificial Sequence
<220> FEATURE:
<223> OTHER INFORMATION: oligonucleotide ZC22916

<400> SEQUENCE: 12
gtaaaccgcc gtccaccaac gcaggtcgtc gtcagaaaca                              40

<210> SEQ ID NO 13
<211> LENGTH: 40
<212> TYPE: DNA
<213> ORGANISM: Artificial Sequence
<220> FEATURE:
<223> OTHER INFORMATION: oligonucleotide ZC22961

<400> SEQUENCE: 13
gttttcacga gcacttcacc aacaaggacc atagattatg                              40

<210> SEQ ID NO 14
<211> LENGTH: 50
<212> TYPE: DNA
<213> ORGANISM: Artificial Sequence
<220> FEATURE:
<223> OTHER INFORMATION: oligonucleotide ZC22962

<400> SEQUENCE: 14
aacaaggacc atagattatg caggatcgcc acatgattcg tatgcgtcag                   50

<210> SEQ ID NO 15
<211> LENGTH: 50
<212> TYPE: DNA
<213> ORGANISM: Artificial Sequence
<220> FEATURE:
<223> OTHER INFORMATION: oligonucleotide ZC22963

<400> SEQUENCE: 15
gtttttcagc tgatcaacaa tatcgatcag ctgacgcata cgaatcatgt                   50

<210> SEQ ID NO 16
<211> LENGTH: 60
<212> TYPE: DNA
<213> ORGANISM: Artificial Sequence
<220> FEATURE:
<223> OTHER INFORMATION: oligonucleotide ZC22964

<400> SEQUENCE: 16
tatgtgaacg acctggttcc ggaattcctg ccggctccgg aagatgttga gaccaactgt       60

<210> SEQ ID NO 17
<211> LENGTH: 60
<212> TYPE: DNA
<213> ORGANISM: Artificial Sequence
<220> FEATURE:

<223> OTHER INFORMATION: oligonucleotide ZC22965

<400> SEQUENCE: 17
tcagctgggc tttctggaaa caggagaaag cggaccactc acagttggtc tcaacatctt    60

<210> SEQ ID NO 18
<211> LENGTH: 60
<212> TYPE: DNA
<213> ORGANISM: Artificial Sequence
<220> FEATURE:
<223> OTHER INFORMATION: oligonucleotide ZC22966

<400> SEQUENCE: 18
tttccagaaa gcccagctga atccgcaaa caccggtaac aacgaacgta tcatcaacgt    60

<210> SEQ ID NO 19
<211> LENGTH: 60
<212> TYPE: DNA
<213> ORGANISM: Artificial Sequence
<220> FEATURE:
<223> OTHER INFORMATION: oligonucleotide ZC22967

<400> SEQUENCE: 19
gttggtggac ggcggtttac gtttcagttt tttaatggaa acgttgatga tacgttcgtt    60

<210> SEQ ID NO 20
<211> LENGTH: 60
<212> TYPE: DNA
<213> ORGANISM: Artificial Sequence
<220> FEATURE:
<223> OTHER INFORMATION: oligonucleotide ZC22968

<400> SEQUENCE: 20
gcaggtcgtc gtcagaaaca ccgtctgacc tgcccgtcct gtgattctta tgagaaaaaa    60

<210> SEQ ID NO 21
<211> LENGTH: 60
<212> TYPE: DNA
<213> ORGANISM: Artificial Sequence
<220> FEATURE:
<223> OTHER INFORMATION: oligonucleotide ZC22969

<400> SEQUENCE: 21
gcagcaggga tttgaaacgt tccaggaatt ctttcggcgg ttttttctca taagaatcac    60

<210> SEQ ID NO 22
<211> LENGTH: 60
<212> TYPE: DNA
<213> ORGANISM: Artificial Sequence
<220> FEATURE:
<223> OTHER INFORMATION: oligonucleotide ZC22970

<400> SEQUENCE: 22
acgtttcaaa tccctgctgc agaaaatgat tcaccagcac ctgtcctctc gtacccacgg    60

<210> SEQ ID NO 23
<211> LENGTH: 60
<212> TYPE: DNA
<213> ORGANISM: Artificial Sequence
<220> FEATURE:
<223> OTHER INFORMATION: oligonucleotide ZC22971

<400> SEQUENCE: 23
aatcttatct catccgccaa acatcagga atcttcggaa ccgtgggtac gagaggacag    60

<210> SEQ ID NO 24
<211> LENGTH: 40
<212> TYPE: DNA
<213> ORGANISM: Artificial Sequence
<220> FEATURE:
<223> OTHER INFORMATION: oligonucleotide ZC22972

<400> SEQUENCE: 24
ttaatctgta tcaggctgaa atcttatct catccgccaa                              40

<210> SEQ ID NO 25
<211> LENGTH: 63
<212> TYPE: DNA
<213> ORGANISM: Artificial Sequence
<220> FEATURE:
<223> OTHER INFORMATION: oligonucleotide ZC40133

<400> SEQUENCE: 25
ctcaacatct tccggagccg gcaggaattc cggaaccagg tcattcacat aattttttcag      60 ctg                                                                    63

<210> SEQ ID NO 26
<211> LENGTH: 64
<212> TYPE: DNA
<213> ORGANISM: Artificial Sequence
<220> FEATURE:
<223> OTHER INFORMATION: oligonucleotide ZC40107

<400> SEQUENCE: 26
ttatagatat tgttgatcag ctgaaaaatt atgtgaatga cctggttccg gaattcctgc      60
cggc                                                                   64

<210> SEQ ID NO 27
<211> LENGTH: 405
<212> TYPE: DNA
<213> ORGANISM: Artificial Sequence
<220> FEATURE:
<223> OTHER INFORMATION: optimized IL-21
<220> FEATURE:
<221> NAME/KEY: CDS
<222> LOCATION: (1)...(405)

<400> SEQUENCE: 27

```
atg caa ggt caa gat cgc cac atg att aga atg cgt caa ctt ata gat        48
Met Gln Gly Gln Asp Arg His Met Ile Arg Met Arg Gln Leu Ile Asp
 1               5                  10                  15 att gtt gat cag ctg aaa aat tat gtg aat gac ctg gtt ccg gaa ttc        96
Ile Val Asp Gln Leu Lys Asn Tyr Val Asn Asp Leu Val Pro Glu Phe
             20                  25                  30 ctg ccg gct ccg gaa gat gtt gag acc aac tgt gag tgg tcc gct ttc       144
Leu Pro Ala Pro Glu Asp Val Glu Thr Asn Cys Glu Trp Ser Ala Phe
         35                  40                  45 tcc tgt ttc cag aaa gcc cag ctg aaa tcc gca aac acc ggt aac aac       192
Ser Cys Phe Gln Lys Ala Gln Leu Lys Ser Ala Asn Thr Gly Asn Asn
     50                  55                  60 gaa cgt atc atc aac gtt tcc att aaa aaa ctg aaa cgt aaa ccg ccg       240
Glu Arg Ile Ile Asn Val Ser Ile Lys Lys Leu Lys Arg Lys Pro Pro
 65                  70                  75                  80 tcc acc aac gca ggt cgt cgt cag aaa cac cgt ctg acc tgc ccg tcc       288
Ser Thr Asn Ala Gly Arg Arg Gln Lys His Arg Leu Thr Cys Pro Ser
                 85                  90                  95 tgt gat tct tat gag aaa aaa ccg ccg aaa gaa ttc ctg gaa cgt ttc       336
Cys Asp Ser Tyr Glu Lys Lys Pro Pro Lys Glu Phe Leu Glu Arg Phe
            100                 105                 110
```

```
aaa tcc ctg ctg cag aaa atg att cac cag cac ctg tcc tct cgt acc    384
Lys Ser Leu Leu Gln Lys Met Ile His Gln His Leu Ser Ser Arg Thr
        115                 120                 125 cac ggt tcc gaa gat tcc tga                                        405
His Gly Ser Glu Asp Ser  *
    130
```

<210> SEQ ID NO 28
<211> LENGTH: 134
<212> TYPE: PRT
<213> ORGANISM: Artificial Sequence
<220> FEATURE:
<223> OTHER INFORMATION: optimized IL-21

<400> SEQUENCE: 28

```
Met Gln Gly Gln Asp Arg His Met Ile Arg Met Arg Gln Leu Ile Asp
 1               5                  10                  15

Ile Val Asp Gln Leu Lys Asn Tyr Val Asn Asp Leu Val Pro Glu Phe
            20                  25                  30

Leu Pro Ala Pro Glu Asp Val Glu Thr Asn Cys Glu Trp Ser Ala Phe
        35                  40                  45

Ser Cys Phe Gln Lys Ala Gln Leu Lys Ser Ala Asn Thr Gly Asn Asn
    50                  55                  60

Glu Arg Ile Ile Asn Val Ser Ile Lys Lys Leu Lys Arg Lys Pro Pro
65                  70                  75                  80

Ser Thr Asn Ala Gly Arg Arg Gln Lys His Arg Leu Thr Cys Pro Ser
                85                  90                  95

Cys Asp Ser Tyr Glu Lys Lys Pro Pro Lys Glu Phe Leu Glu Arg Phe
            100                 105                 110

Lys Ser Leu Leu Gln Lys Met Ile His Gln His Leu Ser Ser Arg Thr
        115                 120                 125

His Gly Ser Glu Asp Ser
    130
```

<210> SEQ ID NO 29
<211> LENGTH: 64
<212> TYPE: DNA
<213> ORGANISM: Artificial Sequence
<220> FEATURE:
<223> OTHER INFORMATION: oligonucleotide ZC43,586

<400> SEQUENCE: 29

```
acaatttcac acagaattca ttaaagagga gaaattaact atggatatta atactgaaac    60
tgag                                                                 64
```

<210> SEQ ID NO 30
<211> LENGTH: 64
<212> TYPE: DNA
<213> ORGANISM: Artificial Sequence
<220> FEATURE:
<223> OTHER INFORMATION: oligonucleotide ZC43,587

<400> SEQUENCE: 30

```
tctgtatcag gctgaaaatc ttatctcatc cgccaaaaca tcatcgccat tgctccccaa    60
atac                                                                 64
```

<210> SEQ ID NO 31
<211> LENGTH: 1965
<212> TYPE: DNA
<213> ORGANISM: Artificial Sequence
<220> FEATURE:
<223> OTHER INFORMATION: DNA sequence of the Red Recombinase operon
      amplified with ZC43,586 and ZC43,587

<400> SEQUENCE: 31

| | | |
|---|---|---|
| acaatttcac acagaattca ttaaagagga gaaattaact atgGatatta atactgaaac | 60 |
| tgagatcaag caaaagcatt cactaacccc ctttcctgtt ttcctaatca gcccggcatt | 120 |
| tcgcgggcga tattttcaca gctatttcag gagttcagcc atgaacgctt attacattca | 180 |
| ggatcgtctt gaggctcaga gctgggcgcg tcactaccag cagctcgccc gtgaagagaa | 240 |
| agaggcagaa ctggcagacg catggaaaa aggcctgccc cagcacctgt ttgaatcgct | 300 |
| atgcatcgat catttgcaac gccacggggc cagcaaaaaa tccattaccc gtgcgtttga | 360 |
| tgacgatgtt gagtttcagg agcgcatggc agaacacatc cggtacatgg ttgaaaccat | 420 |
| tgctcaccac caggttgata ttgattcaga ggtataaaac gaatgagtac tgcactcgca | 480 |
| acgctggctg ggaagctggc tgaacgtgtc ggcatggatt ctgtcgaccc acaggaactg | 540 |
| atcaccactc ttcgccagac ggcatttaaa ggtgatgcca gcgatgcgca gttcatcgca | 600 |
| ttactgatcg ttgccaacca gtacggcctt aatccgtgga cgaaagaaat ttacgccttt | 660 |
| cctgataagc agaatggcat cgttccggtg gtgggcgttg atggctggtc ccgcatcatc | 720 |
| aatgaaaacc agcagtttga tggcatggac tttgagcagg acaatgaatc ctgtacatgc | 780 |
| cggatttacc gcaaggaccg taatcatccg atctgcgtta ccgaatggat ggatgaatgc | 840 |
| cgccgcgaac cattcaaaac tcgcgaaggc agagaaatca cggggccgtg gcagtcgcat | 900 |
| cccaaacgga tgttacgtca taaagccatg attcagtgtg cccgtctggc cttcggattt | 960 |
| gctggtatct atgacaagga tgaagccgag cgcattgtcg aaaatactgc atacactgca | 1020 |
| gaacgtcagc cggaacgcga catcactccg gttaacgatg aaaccatgca ggagattaac | 1080 |
| actctgctga tcgccctgga taaaacatgg gatgacgact tattgccgct ctgttcccag | 1140 |
| atatttcgcc gcgacattcg tgcatcgtca gaactgacac aggccgaagc agtaaaagct | 1200 |
| cttggattcc tgaaacagaa agccgcgagg cagaaggtgg cagcatgaca ccggacatta | 1260 |
| tcctgcagcg taccgggatc gatgtgagag ctgtcgaaca gggggatgat gcgtggcaca | 1320 |
| aattacggct cggcgtcatc accgcttcag aagttcacaa cgtgatagca aaacccgct | 1380 |
| ccggaaagaa gtggcctgac atgaaaatgt cctacttcca cccctgctt gctgaggttt | 1440 |
| gcaccggtgt ggctccggaa gttaacgcta aagcactggc ctggggaaaa cagtacgaga | 1500 |
| acgacgccag aaccctgttt gaattcactt ccggcgtgaa tgttactgaa tccccgatca | 1560 |
| tctatcgcga cgaaagtatg cgtaccgcct gctctcccga tggtttatgc agtgacggca | 1620 |
| acggccttga actgaaatgc ccgtttacct cccgggattt catgaagttc cggctcggtg | 1680 |
| gtttcgaggc cataaagtca gcttacatgg cccaggtgca gtacagcatg tgggtgacgc | 1740 |
| gaaaaaatgc ctggtacttt gccaactatg acccgcgtat gaagcgtgaa ggcctgcatt | 1800 |
| atgtcgtgat tgagcgggat gaaaagtaca tggcgagttt tgacgagatc gtgccggagt | 1860 |
| tcatcgaaaa aatggacgag gcactggctg aaattggttt tgtatttggg gagcaatggc | 1920 |
| gatgatgttt tggcggatga gataagattt tcagcctgat acaga | 1965 |

<210> SEQ ID NO 32
<211> LENGTH: 92
<212> TYPE: DNA
<213> ORGANISM: Artificial Sequence
<220> FEATURE:
<223> OTHER INFORMATION: oligonucleotide ZC45,112

<400> SEQUENCE: 32
attgttacat tgaaatggct agttattccc cggggcgatt ttcacctcgg ggaaatttta    60
gttggcgttc tcaggtcgag gtggcccggc tc    92

<210> SEQ ID NO 33
<211> LENGTH: 99
<212> TYPE: DNA
<213> ORGANISM: Artificial Sequence
<220> FEATURE:
<223> OTHER INFORMATION: oligonucleotide ZC45,171

<400> SEQUENCE: 33
taattgactc attaagttag atataaaaaa tacatattca atcattaaaa cgattgaatg    60
gagaactttt attattgaag catttatcag ggttattgt    99

<210> SEQ ID NO 34
<211> LENGTH: 1591
<212> TYPE: DNA
<213> ORGANISM: Artificial Sequence
<220> FEATURE:
<223> OTHER INFORMATION: Tetracycline promoter::tetracycline gene
      (tetp::tet) PCR fragment amplified with ZC45,112
      and ZC45,171

<400> SEQUENCE: 34
taattgactc attaagttag atataaaaaa tacatattca atcattaaaa cgattgaatg    60
gagaactttt attattgaag catttatcag ggttattgtc tcatgagcgg atacatattt   120
gaatgtattt agaaaaataa acaaataggg gttccgcgca catttccccg aaaagtgcca   180
cctgacgtct aagaaaccat tattatcatg acattaacct ataaaaatag gcgtatcacg   240
aggccttctc atgtttgaca gcttatcatc gataagcttt aatgcggtag tttatcacag   300
ttaaattgct aacgcagtca ggcaccgtgt atgaaatcta acaatgcgct catcgtcatc   360
ctcggcaccg tcaccctgga tgctgtaggc ataggcttgg ttatgccggt actgccgggc   420
ctcttgcggg atatcgtcca ttccgacagc atcgccagtc actatggcgt gctgctagcg   480
ctatatgcgt tgatgcaatt tctatgcgca cccgttctcg gagcactgtc cgaccgcttt   540
ggccgccgcc cagtcctgct cgcttcgcta cttggagcca ctatcgacta cgcgatcatg   600
gcgaccacac ccgtcctgtg gatcctctac gccggacgca tcgtggccgg catcaccggc   660
gccacaggtg cggttgctgg cgcctatatc gccgacatca ccgatgggga agatcgggct   720
cgccacttcg ggctcatgag cgcttgtttc ggcgtgggta tggtggcagg ccccgtggcc   780
gggggactgt tgggcgccat ctccttgcat gcaccattcc ttgcggcggc ggtgctcaac   840
ggcctcaacc tactactggg ctgcttccta atgcaggagt cgcataaggg agagcgtcga   900
ccgatgccct tgagagcctt caacccagtc agctccttcc ggtgggcgcg ggcatgact    960 atcgtcgccg cacttatgac tgtcttcttt atcatgcaac tcgtaggaca ggtgccggca   1020
gcgctctggg tcattttcgg cgaggaccgc tttcgctgga gcgcgacgat gatcggcctg   1080
tcgcttgcgg tattcggaat cttgcacgcc ctcgctcaag ccttcgtcac tggtcccgcc   1140
accaaacgtt tcggcgagaa gcaggccatt atcgccggca tggcggccga cgcgctgggc   1200
tacgtcttgc tggcgttcgc gacgcgaggc tggatggcct tccccattat gattcttctc   1260
gcttccggcg gcatcgggat gcccgcgttg caggccatgc tgtccaggca ggtagatgac   1320
gaccatcagg gacagcttca aggatcgctc gcggctctta ccagcctaac ttcgatcact   1380

```
ggaccgctga tcgtcacggc gatttatgcc gcctcggcga gcacatggaa cgggttggca        1440
tggattgtag gcgccgccct ataccttgtc tgcctcccg cgttgcgtcg cggtgcatgg         1500
agccgggcca cctcgacctg agaacgccaa ctaaaatttc cccgaggtga aaatcgcccc        1560
ggggaataac tagccatttc aatgtaacaa t                                       1591
```

<210> SEQ ID NO 35
<211> LENGTH: 32
<212> TYPE: DNA
<213> ORGANISM: Artificial Sequence
<220> FEATURE:
<223> OTHER INFORMATION: oligonucletide ZC45,357

<400> SEQUENCE: 35

```
tcattaagtt agatataaaa aatacatatt ca                                      32
```

<210> SEQ ID NO 36
<211> LENGTH: 29
<212> TYPE: DNA
<213> ORGANISM: Artificial Sequence
<220> FEATURE:
<223> OTHER INFORMATION: oligonucletide ZC45,350

<400> SEQUENCE: 36

```
taattgttac attgaaatgg ctagttatt                                          29
```

<210> SEQ ID NO 37
<211> LENGTH: 27
<212> TYPE: DNA
<213> ORGANISM: Artificial Sequence
<220> FEATURE:
<223> OTHER INFORMATION: oligonucletide ZC45,353

<400> SEQUENCE: 37

```
atgaaatcta acaatgcgct catcgtc                                            27
```

<210> SEQ ID NO 38
<211> LENGTH: 22
<212> TYPE: DNA
<213> ORGANISM: Artificial Sequence
<220> FEATURE:
<223> OTHER INFORMATION: oligonucletide ZC45,355

<400> SEQUENCE: 38

```
tcaggtcgag gtggcccggc tc                                                 22
```

<210> SEQ ID NO 39
<211> LENGTH: 27
<212> TYPE: DNA
<213> ORGANISM: Artificial Sequence
<220> FEATURE:
<223> OTHER INFORMATION: oligonucletide ZC45,354

<400> SEQUENCE: 39

```
tctaccgaga ctttatcgtt tactcct                                            27
```

<210> SEQ ID NO 40
<211> LENGTH: 28
<212> TYPE: DNA
<213> ORGANISM: Artificial Sequence
<220> FEATURE:
<223> OTHER INFORMATION: oligonucletide ZC45,359

<400> SEQUENCE: 40

```
ttaaaatgtg tacttaagac cagcagta                                           28
```

<210> SEQ ID NO 41
<211> LENGTH: 1585
<212> TYPE: DNA
<213> ORGANISM: Artificial Sequence
<220> FEATURE:
<223> OTHER INFORMATION: Sequence of the 1584bp PCR fragment amplified
      with primer set #1 (ZC45,357 and ZC45,350)

<400> SEQUENCE: 41

| | | | | | |
|---|---|---|---|---|---|
| tcattaagtt | agatataaaa | aatacatatt | caatcattaa | acgattgaa | tggagaactt | 60 |
| ttattattga | agcatttatc | agggttattg | tctcatgagc | ggatacatat | ttgaatgtat | 120 |
| ttagaaaaat | aaacaaatag | gggttccgcg | cacatttccc | cgaaaagtgc | cacctgacgt | 180 |
| ctaagaaacc | attattatca | tgacattaac | ctataaaaat | aggcgtatca | cgaggccttc | 240 |
| tcatgtttga | cagcttatca | tcgataagct | ttaatgcggt | agtttatcac | agttaaattg | 300 |
| ctaacgcagt | caggcaccgt | gtatgaaatc | taacaatgcg | ctcatcgtca | tcctcggcac | 360 |
| cgtcaccctg | gatgctgtag | gcataggctt | ggttatgccg | gtactgccgg | gcctcttgcg | 420 |
| ggatatcgtc | cattccgaca | gcatcgccag | tcactatggc | gtgctgctag | cgctatatgc | 480 |
| gttgatgcaa | tttctatgcg | cacccgttct | cggagcactg | tccgaccgct | ttggccgccg | 540 |
| cccagtcctg | ctcgcttcgc | tacttggagc | cactatcgac | tacgcgatca | tggcgaccac | 600 |
| acccgtcctg | tggatcctct | acgccggacg | catcgtggcc | ggcatcaccg | gcgccacagg | 660 |
| tgcggttgct | ggcgcctata | tcgccgacat | caccgatggg | gaagatcggg | ctcgccactt | 720 |
| cgggctcatg | agcgcttgtt | tcggcgtggg | tatggtggca | ggccccgtgg | ccgggggact | 780 |
| gttgggcgcc | atctccttgc | atgcaccatt | ccttgcggcg | gcggtgctca | acggcctcaa | 840 |
| cctactactg | ggctgcttcc | taatgcagga | gtcgcataag | ggagagcgtc | gaccgatgcc | 900 |
| cttgagagcc | ttcaacccag | tcagctcctt | ccggtgggcg | cggggcatga | ctatcgtcgc | 960 |
| cgcacttatg | actgtcttct | ttatcatgca | actcgtagga | caggtgccgg | cagcgctctg | 1020 |
| ggtcattttc | ggcgaggacc | gctttcgctg | gagcgcgacg | atgatcggcc | tgtcgcttgc | 1080 |
| ggtattcgga | atcttgcacg | ccctcgctca | agccttcgtc | actggtcccg | ccaccaaacg | 1140 |
| tttcggcgag | aagcaggcca | ttatcgccgg | catggcggcc | gacgcgctgg | gctacgtctt | 1200 |
| gctggcgttc | gcgacgcgag | gctggatggc | cttccccatt | atgattcttc | tcgcttccgg | 1260 |
| cggcatcggg | atgcccgcgt | tgcaggccat | gctgtccagg | caggtagatg | acgaccatca | 1320 |
| gggacagctt | caaggatcgc | tcgcggctct | taccagccta | acttcgatca | ctggaccgct | 1380 |
| gatcgtcacg | gcgatttatg | ccgcctcggc | gagcacatgg | aacgggttgg | catggattgt | 1440 |
| aggcgccgcc | ctataccttg | tctgcctccc | cgcgttgcgt | cgcggtgcat | ggagccgggc | 1500 |
| cacctcgacc | tgagaacgcc | aactaaaatt | tccccgaggt | gaaaatcgcc | ccggggaata | 1560 |
| actagccatt | tcaatgtaac | aatta | | | | 1585 |

<210> SEQ ID NO 42
<211> LENGTH: 1191
<212> TYPE: DNA
<213> ORGANISM: Artificial Sequence
<220> FEATURE:
<223> OTHER INFORMATION: Sequence of the 1190bp PCR fragment amplified
      with primer set #2 (ZC45,353 and ZC45,355)

<400> SEQUENCE: 42

| | | | | | |
|---|---|---|---|---|---|
| atgaaatcta | acaatgcgct | catcgtcatc | ctcggcaccg | tcaccctgga | tgctgtaggc | 60 |

-continued

```
ataggcttgg ttatgccggt actgccgggc ctcttgcggg atatcgtcca ttccgacagc      120
atcgccagtc actatggcgt gctgctagcg ctatatgcgt tgatgcaatt tctatgcgca      180
cccgttctcg gagcactgtc cgaccgcttt ggccgccgcc cagtcctgct cgcttcgcta      240
cttggagcca ctatcgacta cgcgatcatg gcgaccacac ccgtcctgtg gatcctctac      300
gccggacgca tcgtggccgg catcaccggc gccacaggtg cggttgctgg cgcctatatc      360
gccgacatca ccgatgggga agatcgggct cgccacttcg ggctcatgag cgcttgtttc      420
ggcgtgggta tggtggcagg ccccgtggcc ggggactgt tgggcgccat ctccttgcat       480
gcaccattcc ttgcggcggc ggtgctcaac ggcctcaacc tactactggg ctgcttccta     540
atgcaggagt cgcataaggg agagcgtcga ccgatgccct tgagagcctt caacccagtc     600
agctccttcc ggtgggcgcg gggcatgact atcgtcgccg cacttatgac tgtcttcttt    660
atcatgcaac tcgtaggaca ggtgccggca gcgctctggg tcattttcgg cgaggaccgc    720
tttcgctgga gcgcgacgat gatcggcctg tcgcttgcgg tattcggaat cttgcacgcc    780
ctcgctcaag ccttcgtcac tggtcccgcc accaaacgtt tcggcgagaa gcaggccatt    840
atcgccggca tggcggccga cgcgctgggc tacgtcttgc tggcgttcgc gacgcgaggc    900
tggatggcct tccccattat gattcttctc gcttccggcg gcatcgggat gcccgcgttg    960
caggccatgc tgtccaggca ggtagatgac gaccatcagg gacagcttca aggatcgctc    1020
gcggctctta ccagcctaac ttcgatcact ggaccgctga tcgtcacggc gatttatgcc   1080
gcctcggcga gcacatggaa cgggttggca tggattgtag gcgccgccct ataccttgtc    1140
tgcctccccg cgttgcgtcg cggtgcatgg agccgggcca cctcgacctg a            1191
```